(12) United States Patent
Williams et al.

(10) Patent No.: US 6,689,929 B2
(45) Date of Patent: Feb. 10, 2004

(54) PROCESS FOR THE PRODUCTION OF PARA-XYLENE USING TOLUENE FEEDS AND PRESSURE SWING ADSORPTION

(75) Inventors: Bryce A. Williams, Lisle, IL (US); Jeffrey T. Miller, Naperville, IL (US); Ruth Ann Doyle, Oswego, IL (US); Giorgio Zoia, Chicago, IL (US)

(73) Assignee: BP Corporation North America Inc., Warrenville, IL (US)

( * ) Notice: Subject to any disclaimer, the term of this patent is extended or adjusted under 35 U.S.C. 154(b) by 122 days.

(21) Appl. No.: 09/902,120

(22) Filed: Jul. 10, 2001

(65) Prior Publication Data

US 2002/0068844 A1 Jun. 6, 2002

Related U.S. Application Data

(60) Provisional application No. 60/220,536, filed on Jul. 10, 2000, provisional application No. 60/238,217, filed on Oct. 5, 2000, and provisional application No. 60/289,313, filed on May 8, 2001.

(51) Int. Cl.[7] ............................. C97C 7/12; C97C 5/22
(52) U.S. Cl. ................. 585/825; 585/820; 585/822; 585/826; 585/827; 585/828
(58) Field of Search ................. 585/820, 822, 585/825, 826, 827, 828

(56) References Cited

U.S. PATENT DOCUMENTS

| | | | |
|---|---|---|---|
| 2,985,589 A | 5/1961 | Broughton et al. | 210/34 |
| 2,985,694 A | 5/1961 | Talbot | 260/674 |
| 3,177,265 A | 4/1965 | Lammers | 260/674 |
| 3,201,491 A | 8/1965 | Stine et al. | 260/676 |
| 3,467,724 A | 9/1969 | Laurich | 260/674 |
| 3,626,020 A | 12/1971 | Neuzil | 260/674 |
| 3,653,184 A | 4/1972 | Drinkard | 55/67 |
| 3,656,278 A | 4/1972 | Drinkard et al. | 55/67 |

(List continued on next page.)

FOREIGN PATENT DOCUMENTS

| | | |
|---|---|---|
| CN | 1136549 | 11/1996 |
| EP | 138617 | 4/1985 |
| EP | 923512 | 6/1999 |
| FR | 2757507 | 12/1996 |
| GB | 1420796 | 1/1976 |
| WO | WO9317987 | 9/1993 |
| WO | WO9622262 | 7/1996 |
| WO | WO0069796 | 11/2000 |

OTHER PUBLICATIONS

Namba, S., et al., "Novel purification method of commerical o– and m–xylenes by shape selective adsorption on HZSM–5", Microporous Materials, 8, 39 (1997).

(List continued on next page.)

Primary Examiner—Glenn Caldarola
Assistant Examiner—Tam M. Nguyen
(74) Attorney, Agent, or Firm—Mary Jo Kanady; Thomas A. Yassen

(57) ABSTRACT

A pressure swing adsorption process to separate para-xylene and ethylbenzene from a $C_8$ aromatics stream produced by toluene conversion uses a para-selective adsorbent, preferably a non-acidic, medium pore molecular sieve of the MFI structure type, and is operated isothermally in the vapor phase at elevated temperatures and pressures. A fixed bed of adsorbent is saturated with pX and EB, which are preferentially adsorbed, then the feed to the process is stopped. Lowering the partial pressure desorbs the pX and EB giving a pX/EB-rich effluent. A stream of non-adsorbed mX and oX may be obtained before desorbing pX and EB.

43 Claims, 7 Drawing Sheets

U.S. PATENT DOCUMENTS

| | | | |
|---|---|---|---|
| 3,662,013 A | 5/1972 | Machell et al. | 260/674 |
| 3,696,107 A | 10/1972 | Neuzil | 260/674 |
| 3,699,182 A | 10/1972 | Cattanach | 260/674 |
| 3,724,170 A | 4/1973 | Allen et al. | 55/67 |
| 3,729,523 A | 4/1973 | Grandio, Jr. et al. | 260/674 |
| 3,770,841 A | 11/1973 | Meyers, Jr. | 260/668 |
| 3,960,520 A | 6/1976 | Allen | 55/59 |
| 4,039,599 A | 8/1977 | Gewartowski | 260/674 |
| 4,098,836 A | 7/1978 | Dwyer | 260/668 |
| 4,184,943 A | 1/1980 | Anderson | 208/310 |
| 4,381,419 A | 4/1983 | Wylie | 585/828 |
| 4,402,832 A | 9/1983 | Gerhold | 210/659 |
| 4,453,029 A | 6/1984 | Dessau | 585/828 |
| RE31,782 E | 12/1984 | Olson et al. | 585/481 |
| 4,899,011 A | 2/1990 | Chu et al. | 585/481 |
| 4,899,017 A | 2/1990 | Yan | 585/828 |
| 4,908,342 A | 3/1990 | McWilliams et al. | 502/68 |
| 5,001,296 A | 3/1991 | Howley et al. | 585/489 |
| 5,028,573 A | 7/1991 | Brown et al. | 502/66 |
| 5,284,992 A | 2/1994 | Hotier et al. | 585/805 |
| 5,329,060 A | 7/1994 | Swift | 585/805 |
| 5,367,099 A | 11/1994 | Beck et al. | 585/475 |
| 5,448,055 A | 9/1995 | Nakamura et al. | 250/208 |
| 5,705,726 A | 1/1998 | Abichandani et al. | 585/481 |
| 5,866,740 A | 2/1999 | Mikitenko et al. | 585/470 |
| 5,908,967 A | 6/1999 | Benazzi et al. | 585/481 |
| 5,922,924 A | 7/1999 | Hotier et al. | 585/479 |
| 5,948,950 A | 9/1999 | Hotier et al. | 585/828 |
| 6,051,744 A | 4/2000 | Nacamuli et al. | 585/481 |
| 6,111,161 A | 8/2000 | MacPherson et al. | 585/812 |
| 6,114,592 A | 9/2000 | Gajda et al. | 585/475 |
| 6,147,272 A | 11/2000 | Mikitenko et al. | 585/812 |
| 6,150,292 A | 11/2000 | Merlen et al. | 502/66 |
| 6,573,418 B2 * | 6/2003 | Miller et al. | 585/826 |

OTHER PUBLICATIONS

Yan, T. Y., "Separation of p–Xylene and Ethylbenzene from C8 Aromatics Using Medium–Pore Zeolites", Ind. Eng. Chem. Res., 28,: 572–576 (1989).

Choudhary, V. R., et al., "Single–Component Sorption/Diffusion of Cyclic Compounds from Their Bulk Liquid Phase in H–ZSM–5 Zeolite", Ind. Eng. Chem. Res., 36,: 1812–1818 (1997).

Wu, E. L., et al., "Hydrocarbon Adsorption Characterization of Some High Silica Zeolite", Stud Surf. Sci. Catal. 28, 547 (1996).

* cited by examiner

XYLENE VAPOR PHASE SATURATION CONCENTRATION

PROCESS FOR THE PRODUCTION OF PARA-XYLENE USING TOLUENE FEEDS AND PRESSURE SWING ADSORPTION

This application claims the benefit of U.S. Provisional Application No. 60/220,536 filed Jul. 10, 2000, U.S. Provisional Application No. 60/238,217 filed Oct. 5, 2000, and U.S. Provisional Application No. 60/289,313 filed May 8, 2001, all of which are incorporated herein by reference in their entireties.

BACKGROUND OF THE INVENTION

The present invention relates to a process for producing para-xylene from toluene-containing feeds incorporating pressure swing adsorption and toluene conversion. The present invention includes a pressure swing adsorption (PSA) process component for separating para-xylene and ethylbenzene from mixed $C_8$ aromatics using a non-acidic, medium pore molecular sieve. The molecular sieve is preferably of the MFI structure type and the process is preferably operated in the vapor phase at elevated temperatures and pressures wherein the temperature is substantially isothermal. The present invention also relates to a method of pressure swing adsorption which includes a plurality of steps and which provides recovery from a mixture comprising $C_8$ aromatics of a substantially pure para-xylene or para-xylene and ethylbenzene product stream and a substantially pure meta-xylene and ortho-xylene product stream.

It is known that certain high surface area, porous substances such as silica gel, activated charcoal, and molecular sieves, including zeolites and other molecular sieves, have certain selective adsorption characteristics useful in separating a hydrocarbon mixture into its component parts.

The selective sorption properties of molecular sieves and zeolites have been disclosed in earlier patents and in literature references. Crystalline molecular sieves and zeolites are shape-selective in that they will admit molecules of specific geometry while excluding other molecules.

The separation of xylene isomers has been of particular interest because of the usefulness of para-xylene in the manufacture of terephthalic acid which is used in the manufacture of polyester fabric. Other components of the $C_8$ aromatic hydrocarbon feedstream from which para-xylene (pX) is generally produced are ortho-xylene (oX), which is used in the manufacture of phthalic anhydride which is used to make phthalate based plasticizers; meta-xylene (mX), which is used in the manufacture of isophthalic acid used in the production of specialty polyester fibers, paints, and resins; and ethylbenzene (EB) which is used in the manufacture of styrene.

A refinery feedstock of aromatic $C_8$ mixtures containing ethylbenzene and xylenes will typically have the following content:

| | |
|---|---|
| ethylbenzene | about 0 wt % to about 50 wt % |
| para-xylene | about 0 wt % to about 25 wt % |
| ortho-xylene | about 0 wt % to about 35 wt % |
| meta-xylene | about 20 wt % to about 90 wt % |
| non-aromatics | about 0 wt % to about 10 wt % |
| $C_9^+$ aromatics | about 0 wt % to about 30 wt % |

Equilibrium mixtures of $C_8$ aromatic hydrocarbons generally contain about 22 weight percent para-xylene, about 21 weight percent ortho-xylene, and about 48 weight percent meta-xylene in the equilibrium mixture.

Processes to separate xylene isomers include low temperature crystallization, fractional distillation, selective sulfonation with subsequent hydrolysis and selective solvent separation; however, such processes require high operating costs.

The use of faujasite zeolites, which are large pore type X and Y type zeolites, as adsorbents in liquid phase, chromatographic-type separations is well known.

In the petrochemical production chain, one of the most important streams is the $C_6$ to $C_8$ aromatics stream containing benzene, toluene, and xylenes (BTX), which is a source of raw materials for high value downstream products. Of the $C_8$ aromatics, para-xylene (pX) is the most desirable. However, because the boiling points of ethylbenzene (EB), ortho-xylene (oX), meta-xylene (mX) and para-xylene (collectively referred to as "$C_8$ aromatics") are close, they are difficult to separate by fractional distillation. As a consequence, various alternative methods of separating pX from the $C_8$ aromatics have been developed. Common separation methods are fractional crystallization, which utilizes the difference in freezing points, and liquid phase adsorption (e.g., UOP's Parex process and IFP's Eluxyl process), which uses a faujasite zeolite to chromatographically separate pX from the other $C_8$ aromatics. The reject stream from the crystallization process or the raffinate from the adsorption process are depleted in pX, and contain relatively high proportions of EB, oX and mX. These streams are typically sent to a catalyst reactor, where the xylenes are isomerized to equilibrium, and at least a portion of the EB is converted to other products, which can be removed from the $C_8$ aromatics by fractional distillation.

Processes for making pX have typically included combinations of isomerization with fractional crystallization or adsorption separation. FIG. 1 is a schematic representation of known art combination of an isomerization catalyst reactor and a crystallization unit. Crystallization is a separation process that takes advantage of the fact that pX crystallizes before the other isomers, i.e., pX crystallizes at 13.3° C. (55.9° F.), whereas oX crystallizes at −25.2° C. (13.4° F.) and mX at −47.9° C. (−54.2° F.). In the physical system of the three isomers, there are two binary eutectics of importance, the px/mX and the pX/oX. As pX is crystallized from the mixture, the remaining mixture (mother liquor) composition approaches one of these eutectic binaries, depending on the starting composition of the mixture. Therefore, in commercial practice, pX is crystallized so that the binary eutectic is only approached but not reached to avoid co-crystallization of the xylene isomers, which would lower the pX purity. Thus, the key disadvantage for crystallization is restricted pX recovery per pass, due to this eutectic limit of the $C_8$ stream. Typically, the concentration of pX in a mixed $C_8$ aromatic stream at equilibrium is about 22 wt %. In commercial crystallization operations, the eutectic point of this mixture limits the pX removed per pass to about 65% of that amount.

The problem of the eutectic limit for pX crystallization has been recognized for some time. U.S. Pat. No. 5,329,060 discloses that the eutectic point of the crystallization unit can be overcome by use of a selective adsorption zone that enriches the pX feed to the crystallizer by rejecting most of the mX, oX and EB to the isomerization reactor. Specifically, the disclosure teaches using a faujasite-based, liquid phase adsorption process that can either be selective for pX or selective for mX and oX. The result of this process is a stream enriched in pX, but still containing a substantial portion of mX and oX. Similarly, U.S. Pat. No. 5,922,924 discloses combining at least one liquid phase, simulated moving bed adsorption zone with crystallization to produce high purity pX. Again, pX is enriched, but the stream still contains significant mX and oX.

U.S. Pat. No. 3,699,182 discloses use of zeolite ZSM-5 in a process for selective separation of biphenyls from mixtures containing the same and para-disubstituted aromatic isomers from mixtures containing the same, particularly for separating $C_8$ aromatics using ZSM-5 zeolite.

U.S. Pat. No. 3,724,170 discloses chromatographic separation of C8 aromatic mixtures over zeolite ZSM-5 or ZSM-8, which has preferably been reacted with an organic radical-substituted silane, in at least two distinct stages whereby para-xylene and ethylbenzene are selectively absorbed whereas the meta-xylene and ortho-xylene are not adsorbed, removing the unadsorbed meta-xylene and ortho-xylene, eluting the para-xylene followed by the ethylbenzene.

British Pat. No. 1,420,796 discloses use of zeolite ZSM-5 or ZSM-8, preferably ZSM-5 or ZSM-8 zeolites which have been reacted with certain silanes, for adsorptive separation of para-xylene and ethylbenzene from a mixture of para-xylene, ortho-xylene, meta-xylene, and ethylbenzene by adsorption/desorption using two or more columns operated in a parallel manner so that when adsorption is being conducted in one column, desorption can be conducted in a parallel column under such conditions as to obtain a continuously operating process which is said to have faster results than use of a single column alone. It is stated that 250° C. (482° F.) is a preferred upper limit as operation above 250° C. (482° F.) may lead to catalytic conversion in the zeolite-containing column.

U.S. Pat. No. 3,729,523 discloses a process for separating and recovering each of the xylene isomers and ethylbenzene wherein a mixture of $C_8$ aromatic hydrocarbons, which may also contain $C_9$ and higher paraffins, is heated to 50° F.–500° F. (10° C.–260° C.) and subjected to an adsorption step to recover a first mixture of para-xylene and ethylbenzene and a second mixture comprising meta-xylene, ortho-xylene, and the $C_9$ and higher aromatics. The adsorption is preferably conducted in the presence of a molecular sieve or synthetic crystalline aluminosilicate zeolite as the adsorbent, with ZSM-5, the preferred zeolite. The para-xylene and ethylbenzene are adsorbed and may be recovered by heating the adsorbent, reducing the partial pressure of the sorbed material in the vapor or liquid surrounding the adsorbent, lowering the total pressure of the system or purging with a suitable inert gas or displacement liquid. The resulting para-xylene and ethylbenzene mixture is then subjected to crystallization to recover para-xylene and the mother liquor is subjected to distillation to recover the ethylbenzene.

Chinese Patent Application No. 1136549 discloses selectively adsorbing pX and EB from a $C_8$ isomer stream using silicalite-1 zeolite and then producing >99.5% purity mX and oX from the portion of the stream not adsorbed. In this process there is a substantial amount of contaminating feedstream in the voids of the silicalite-1 adsorbent which is not removed and comes off the adsorption bed along with the adsorbed pX and EB so that the desorbed stream is not substantially pure pX and EB but contains significant amounts of unseparated oX and mX.

None of these references discloses a process using pressure swing adsorption employing a para-selective adsorbent which is preferably a large crystal, non-acidic, medium pore molecular sieve in connection with a toluene conversion component for producing a $C_8$ aromatic feed.

Molecular sieves are crystalline oxides having pore openings and internal cavities the size of some molecules. Zeolites, a sub-group of molecular sieves, are crystalline aluminosilicates. Another well known sub-group of molecular sieves are aluminophosphates or ALPOs. In general, molecular sieves are classified into three groups based on pore size: small pore molecular sieves with pore diameters from 3–4 Å; medium pore molecular sieves with pores diameters from 4–6 Å; and large pore molecular sieves with pore openings of 6–8 Å. In addition to the molecular size pores, molecular sieves have high adsorption energies and for many years have been used as adsorbents. By selection of the proper pore size, molecular sieves may selectively adsorb molecules of different size. This molecular sieving leads to adsorption and separation of the smaller molecule. Often molecular sieving selectivities are high, 100 or greater. The separation of branched from linear paraffins is a commercial process, which utilizes the small pore A zeolite.

Large pore molecular sieves have also been utilized in the separation of hydrocarbons. In large pore molecular sieves, however, all components diffuse into the pores and the separation is based on differences in adsorption energies. The molecule with the highest bond energy is preferentially adsorbed. Generally, adsorption selectivities are high only when molecules have very different heats of adsorption, for example water and paraffin. For molecules with similar heats of adsorption, the adsorption selectivities are low, ca. 1–4. Xylenes isomers, for example, have similar heats of adsorption in Y zeolite. Due to small differences in heats of adsorption and packing geometry in BaY, pX displays an adsorption selectivity of about 2 compared with the other $C_8$ aromatics. In order to separate pX in sufficient purity for chemical sale, i.e., greater than 99%, many separation stages must be conducted. This type of process operates on principles similar to that of chromatography. Commercial examples of separations of this type are the UOP Parex and IFP Eluxyl liquid phase adsorption processes, which utilize ion exchanged Y zeolites to separate pX from $C_8$ aromatics.

Adsorbents useful in the present invention are based on molecular sieves that selectively adsorb p-xylene within the channels and pores of the molecular sieve while not effectively adsorbing m-xylene and o-xylene $C_8$ isomers (i.e., total exclusion of the larger m-xylene and o-xylene or having much slower adsorption rates compared to p-xylene.).

Molecular sieves are ordered porous crystalline materials, typically formed from silica, alumina, and phosphorus oxide ($PO_4$) tetrahedra, that contain a crystalline structure with cavities interconnected by channels. The cavities and channels within the crystalline structure are uniform in size and may permit selective separation of hydrocarbons based upon molecular dimensions. Generally, the term "molecular sieve" includes a wide variety of natural and synthetic crystalline porous materials which typically are based on silica tetrahedra in combination with other tetrahedral oxide materials such as aluminum, boron, titanium, iron, gallium, and the like. In these structures networks of silicon and elements such as aluminum are cross-linked through sharing of oxygen atoms. Substitution of elements such as aluminum or boron for silicon in the molecular sieve structure produces a negative framework charge which must be balanced with positive ions such as alkali metal, alkaline earth metal, ammonium or hydrogen. Molecular sieve structures also may be formed based on phosphates in combination with other tetrahedrally substituted elements such as aluminum.

Adsorbents useful in this invention should not possess catalytic isomerization or conversion activity with respect to the $C_8$ aromatic feedstream. Thus, suitable molecular sieves should be non-acidic. If an element such as aluminum or gallium is substituted in the molecular sieve framework, the sieve should be exchanged with a non-acidic counter-ion, such as sodium, to create a non-acidic sieve adsorbent.

Examples of molecular sieves suitable as adsorbents useful in this invention include zeolitic materials containing pore dimensions in the range of 5 to 6 Å (10–8 meter), typically 5.1 to 5.7 Å, and preferably 5.3 to 5.6 Å, as measured in cross axes of the pore. This range typically is referred to as "medium pore" and typically contains 10-ring tetrahedra structures. Typical examples of medium pore molecular sieves include those with MFI and MEL framework structures as classified in Meier and Olson, "Atlas of Zeolite Structure Types," International Zeolite Association (1987), incorporated herein by reference in its entirety. A small pore molecular sieve, such as A zeolite, which contains 8-ring structures does not have a sufficiently large pore opening to effectively adsorb para-xylene within the sieve. Most large pore molecular sieves, such as mordenite, Beta, LTL, or Y zeolite, that contain 12-ring structures do not adsorb para-xylene selectively with respect to ortho- and meta-xylenes. However, several 12 ring structures, having a smaller effective pore size, for example due to puckering, are potentially useful in the invention, such as structure types MTW (e.g., ZSM-12) and ATO (e.g., ALPO-31).

Specific examples of molecular sieves include ZSM-5 (MFI structure type) and ZSM-11 (MEL structure type) and related isotypic structures. Since suitable adsorbents should not be catalytically reactive to components in the feedstream, the preferable adsorbent useful in this invention is silicalite (MFI structure type), an essentially all silica molecular sieve, which contains minimal amounts of aluminum or other substituted elements. Typically, the silica/alumina ratio of suitable silicalite is above 200 and may range above 1000 depending on the contaminant level of aluminum used in the sieve's preparation. Other MFI and MEL sieves may be used to the extent they are made non-catalytically active. MFI-based molecular sieves are preferred in this invention with silicalite as the most preferred. Other potentially useful adsorbents include structure types MTT, FER, EUO, MFS, TON, AEL, ATO, NES, and others with similar pore sizes.

A molecular sieve which is not catalytically reactive will typically exhibit less than 10% conversion of pX to mX and oX, and preferably less than 5%, and most preferably less than 1%, at the temperature of operation for the process of the invention.

Attempts have been made to use adsorption with zeolites such as ZSM-5 and ZSM-8 to separate ethylbenzene (EB), para-xylene (pX), meta-xylene (mX), and ortho-xylene (oX) from mixtures of $C_8$ aromatics; however, a major disadvantage of these processes is that the time required to effect desorption of the adsorbed components is too long to provide a commercially useful process. In addition, with acidic zeolites, such as HZSM-5, the high temperatures used to obtain rapid desorption cause catalytic reactions to occur converting pX to mX and oX and converting EB to benzene. Furthermore, with HZSM-5, traces of olefins, which are usually present in commercial feeds, irreversibly chemisorb lowering the adsorption capacity of the zeolite. As a result, frequent reconditioning of the adsorbent (e.g., removal of coke deposits) is required.

Due to the strong adsorption and reactivity of xylenes on acid sites of adsorbents such as HZSM-5, a commercial separation process has not been developed. We describe the use of silicalite in a high temperature process to effect the separation of para-xylene and ethylbenzene from a $C_8$ aromatic mixture without reaction of the adsorbed hydrocarbons. These adsorbent and process modifications solve the previous technical obstacles, which have limited commercial development of a molecular sieving, selective adsorption/desorption process for separation of $C_8$ aromatic hydrocarbons.

The process of the present invention overcomes disadvantages of known processes by using pressure swing adsorption at elevated temperature and pressure with a non-acidic, molecular sieve-containing adsorbent to accomplish a rapid adsorption and desorption of the desired components from a feedstream containing $C_8$ aromatics and provide a rapid separation of the desired components which is suitable for commercial use. A non-acidic molecular sieve, such as silicalite (MFI structure type with little to no aluminum), is used to selectively adsorb pX and EB. Desorption is significantly faster and reactions of the adsorbed molecules (pX and EB) do not occur. In addition, olefins do not adsorb on the silicalite, so the adsorption capacity of the adsorbent remains high and frequent reconditioning is not required.

Many of the chemical and physical properties of xylene isomers and ethylbenzene are very similar making separation difficult. The molecular size of these isomers, however, is slightly different and is determined by the position of methyl substitution. The kinetic diameter of para-xylene and ethylbenzene are approximately 6.0 Å; whereas meta-xylene and ortho-xylene are slightly larger, 6.8 Å. It has been known for many years that, based on these differences in size, medium pore zeolites, such as HZSM-5, can selectively adsorb para-xylene and ethylbenzene [See U.S. Pat. Nos. 3,653,184; 3,656,278; 3,770,841; 3,960,520; 4,453,029; 4,899,017; Wu, et al. STUD. SURF. SCI. CATAL., 28:547 (1996); Yan, T. Y., IND. ENG. CHEM. RES. 28:572(1989); and Choudhary, et al., IND. ENG. CHEM. RES. 36:1812 (1997)] However, a disadvantage of using HZSM-5 for such separations is that protonation of the aromatic ring by acid sites in ZSM-5 leads to formation of a strong chemical bond [Farneth, et al., LANGMUIR, 4:152(1988)] resulting in low desorption rates and long desorption times at low temperature. As a result, such excessively large amounts of ZSM-5 would be required for commercial scale separation of para-xylene and ethylbenzene under these conditions that such separations are not commercially feasible. Increasing the desorption temperature does increase the desorption rate, which lowers the amount of adsorbent needed; however, the acid sites on the HZSM-5 zeolite also have catalytic properties which cause undesirable isomerization of para-xylene to meta-xylene and ortho-xylene, significantly reducing para-xylene purity. Another disadvantage is that the acid sites strongly adsorb olefins which are typically present along with the $C_8$ aromatics in the feedstream, thus lowering the capacity of the adsorbent to adsorb para-xylene and ethylbenzene. These olefins can only be desorbed at high temperatures. Thus, there is either a loss of adsorption capacity at low temperature or a loss in selectivity at high temperature due to reactions catalyzed by the acid sites.

Disadvantages of the earlier processes are overcome in the present invention by using a pressure swing adsorption process for separating para-xylene and ethylbenzene from mixed $C_8$ aromatics using a non-acidic, medium pore molecular sieve, preferably of the MFI structure type and preferably operating in the vapor phase at elevated temperatures and pressures.

We have found that non-acidic forms of ZSM-5, such as Na-ZSM-5, are preferred adsorbents over HZSM-5. In particular, silicalite is a preferred adsorbent over HZSM-5. Silicalite, an all silica, isostructural form of ZSM-5 has been shown to possess superior properties. Like ZSM-5, silicalite selectively adsorbs pX and EB; however, desorption is significantly faster, since the molecules are only adsorbed physically not chemically, as with HZSM-5. Moreover, pX does not isomerize, even at the elevated temperatures necessary to make the process economically practicable.

In silicalite, a silica analog of H-ZSM-5, pX and EB are selectively adsorbed due to their smaller size. However, unlike H-ZSM-5, silicalite contains no acid sites. As a result, pX and EB are desorbed at high temperature without reaction. At elevated temperature, the desorption rates are high and the cycle times are much shorter. As a result, much less adsorbent is required. Furthermore, the adsorption capacity does not decrease significantly with repeated adsorption/desorption cycles due to adsorption of olefins in the aromatic stream.

The PSA component of the present invention uses selective adsorption (adsorption of the smaller $C_8$ isomers) and selective desorption (i.e., no isomerization upon desorption) at substantially isothermal temperatures to provide a substantially pure product stream of para-xylene and ethylbenzene and a substantially pure stream of ortho-xylene and meta-xylene. The components in these streams can be further separated to provide substantially pure para-xylene, ethylbenzene, ortho-xylene, and meta-xylene products.

The problems of long desorption times or the need for excessively large amounts of adsorbent have made earlier attempts to separate C8 aromatics by molecular sieving commercially impracticable. In addition to these disadvantages, there is also the problem of how to remove $C_8$ aromatic feed that collects in non-selective voids, that is, feed which collects in the non-selective void volume (i.e., large mesopores in the adsorbent, interstitial space between adsorbent particles, and void space in the adsorbent vessel) so that the purity of the desorbed product stream will not be reduced by this material. The art has not recognized how to overcome this problem for $C_8$ aromatics.

The present invention has solved this problem by selectively separating the $C_8$ aromatic feed that is contained in the non-selective void volume so that a high purity stream of para-xylene and ethylbenzene is obtained following desorption. A high purity stream of mX and oX is also obtained by the process of the invention. In one embodiment of the invention this high purity stream of mX/oX is obtained by separating the mX/oX from the non-selective void volume prior to desorbing the pX/EB.

The use of the process of the present invention in para-xylene production facilities would significantly reduce the amount of meta-xylene and ortho-xylene sent to a crystallization section or a simulated moving bed liquid chromatography section, thus opening up capacity and decreasing operating costs. This would increase the para-xylene concentration and yields. Having a stream with a greater concentration of para-xylene going to the crystallization section may also make it possible to eliminate a crystallizer, for example, a low-temperature ethylene unit might not be needed if a feed with a higher concentration of para-xylene is being crystallized to recover para-xylene. This would also save equipment costs and reduce the amount of energy necessary to conduct the crystallization and purification of para-xylene.

The present invention is a process for producing para-xylene from toluene-containing feeds which incorporates toluene conversion with pressure swing adsorption. This invention comprises a process for the production of para-xylene using a pressure-swing adsorption (PSA) process disclosed herein, in combination with toluene-based processes for the production of para-xylene. The main advantage is that both crystallization and simulated moving bed adsorption chromatography (SiMBAC) are most efficiently operated when used to purify a concentrated stream of PX. The PSA technology can perform such a bulk separation to further concentrate a PX-containing stream before, optionally, sending a more concentrated PX stream to crystallization or SiMBAC. With such a process, portions of the various separation processes can be redesigned to decrease both capital and operating costs. In addition, the overall yield of PX will be improved by using the PSA technology.

SUMMARY OF THE INVENTION

The present invention relates to a pressure swing adsorption (PSA) process for separating para-xylene, or para-xylene and ethylbenzene, from a mixture containing $C_8$ aromatics produced by conversion of a toluene-containing feedstream. The present invention is a process for producing para-xylene from a toluene feed which integrates pressure swing adsorption and toluene conversion. The present invention includes a pressure swing adsorption (PSA) process component for separating para-xylene and ethylbenzene from mixed $C_8$ aromatics using a para-selective adsorbent, preferably a para-selective, non-acidic molecular sieve, more preferably a para-selective, non-acidic, medium pore molecular sieve, and a toluene conversion component for producing a C8 aromatic feed that is separated by means of pressure swing adsorption. Generally the $C_8$ aromatic feedstream from the toluene conversion component will be separated from unreacted toluene by distillation, crystallization, or simulated moving bed chromatography prior to being subjected to PSA.

The PSA component of the present invention relates to a method for separating para-xylene from a gaseous feed mixture containing meta-xylene and ortho-xylene under substantially isothermal conditions comprising:

(a) adsorbing the mixture onto an adsorbent containing a para-selective adsorbent capable of selectively adsorbing para-xylene at a temperature and pressure at which at least 0.01 grams of para-xylene may be adsorbed per gram of para-selective adsorbent;

(b) producing a first effluent stream containing a mixture of ortho-xylene and meta-xylene, having no more than a total of about 20 mole percent of para-xylene based on total $C_8$ aromatics, preferably less than about 20 mole percent of para-xylene, more preferably no more than about 15 mole percent of para-xylene, more preferably less than about 15 mole percent of para-xylene, more preferably no more than about 10 mole percent of para-xylene, more preferably less than about 10 mole percent of para-xylene, more preferably no more than about 5 mole percent of para-xylene, more preferably less than about 5 mole percent of para-xylene, more preferably no more than about 3 mole percent of para-xylene, more preferably less than about 3 mole percent of para-xylene, more preferably no more than about 1 mole percent of para-xylene, and most preferably less than about 1 mole percent of para-xylene based on total $C_8$ aromatics;

(c) selectively removing feed from the non-selective void volume;

(d) selectively desorbing para-xylene by decreasing partial pressure of para-xylene; and (e) collecting a stream containing para-xylene and having no more than a total of about 50 mole percent of meta-xylene and ortho-xylene based on total $C_8$ aromatics; preferably less than about 50 mole percent of meta-xylene and ortho-xylene, more preferably no more than about 45 mole percent of meta-xylene and ortho-xylene, more preferably less than about 45 mole percent of meta-xylene and ortho-xylene, more preferably no more than about 40 mole percent of meta-xylene and ortho-xylene, preferably less than about 40 mole percent of meta-xylene and ortho-xylene, more preferably no more than about 35 mole percent of meta-xylene and ortho-xylene, more preferably less than about 35 mole percent of meta-xylene and ortho-xylene, more preferably no more than about 30 mole percent of meta-xylene and ortho-xylene, more preferably less than about 30 mole percent of meta-xylene and ortho-xylene, more preferably no more than about 25 mole percent of meta-xylene and ortho-xylene, more preferably less than about 25 mole percent of meta-xylene and ortho-xylene, more preferably no more than about 20 mole percent of meta-xylene and ortho-xylene, more preferably less than about 20 mole percent of meta-xylene and ortho-xylene, more preferably no more than about 15 mole percent of meta-xylene and ortho-xylene, more preferably less than about 15 mole percent of meta-xylene and ortho-xylene, more preferably no more than about 10 mole percent of para-xylene, more preferably less than about 10 mole percent of meta-xylene and ortho-xylene, more preferably no more than about 5 mole percent of meta-xylene and ortho-xylene, and most preferably less than about 5 mole percent of meta-xylene and ortho-xylene based on total $C_8$ aromatics.

A practice of the invention involves principally proceeding by repeated cycles comprising in an individual cycle the above steps (a) through (e).

Additional embodiments of the PSA component of the process of the present invention are described below.

In step (a) of the process of the present invention described above, it is preferable that at least 0.01 g of para-xylene be adsorbed per gram of para-selective adsorbent contained in the adsorbent; more preferable that at least 0.02 g of para-xylene be adsorbed per gram of para-selective adsorbent contained in the adsorbent; and even more preferable that at least 0.03 g of para-xylene be adsorbed per gram of para-selective adsorbent contained in the adsorbent.

Preferably, the first effluent stream mixture of ortho-xylene and meta-xylene produced in the process of the invention, as, for example, in step (b) above, will contain no more than about 20 mole percent of para-xylene based on total $C_8$ aromatics, preferably less than about 20 mole percent of para-xylene, more preferably no more than about 15 mole percent of para-xylene, more preferably less than about 15 mole percent of para-xylene, more preferably no more than about 10 mole percent of para-xylene, more preferably less than about 10 mole percent of para-xylene, more preferably no more than about 5 mole percent of para-xylene, more preferably less than about 5 mole percent of para-xylene, more preferably no more than about 3 mole percent of para-xylene, more preferably less than about 3 mole percent of para-xylene, and still more preferably no more than about 1 mole percent of para-xylene, and even more preferably less than about 1 mole percent of para-xylene.

Preferably, the para-xylene-containing stream collected in the process of the invention, as, for example, in step (e) above, will contain no more than a total of about 50 mole percent of meta-xylene and ortho-xylene based on total $C_8$ aromatics, preferably less than a total of about 50 mole percent of meta-xylene and ortho-xylene, more preferably no more than a total of about 45 mole percent of meta-xylene and ortho-xylene, preferably less than a total of about 45 mole percent of meta-xylene and ortho-xylene, more preferably no more than a total of about 40 mole percent of meta-xylene and ortho-xylene, preferably less than a total of about 40 mole percent of meta-xylene and ortho-xylene, more preferably no more than a total of about 30 mole percent of meta-xylene and ortho-xylene, preferably less than a total of about 30 mole percent of meta-xylene and ortho-xylene, preferably no more than a total of about 25 mole percent of meta-xylene and ortho-xylene; preferably less than a total of about 25 mole percent of meta-xylene and ortho-xylene; more preferably no more than a total of about 20 mole percent of meta-xylene and ortho-xylene, preferably less than a total of about 20 mole percent of meta-xylene and ortho-xylene, more preferably no more than a total of about 15 mole percent of meta-xylene and ortho-xylene, preferably less than a total of about 15 mole percent of meta-xylene and ortho-xylene, more preferably no more than a total of about 10 mole percent of meta-xylene and ortho-xylene, preferably less than a total of about 10 mole percent of meta-xylene and ortho-xylene, more preferably no more than a total of about 5 mole percent of meta-xylene and ortho-xylene, and most preferably less than a total of about 5 mole percent of meta-xylene and ortho-xylene based on total $C_8$ aromatics.

In the most preferred embodiments of the invention, the effluent product stream containing para-xylene, or para-xylene and ethylbenzene, will be substantially free of meta-xylene and ortho-xylene, and the effluent product stream containing meta-xylene and ortho-xylene will be substantially free of para-xylene, or substantially free of para-xylene and ethylbenzene.

The adsorbent is preferably a para-selective adsorbent, more preferably a para-selective, non-acidic molecular sieve, more preferably a para-selective, non-acidic, medium pore molecular sieve. Preferably, the molecular sieve comprises silicalite, and more preferably, the molecular sieve comprises orthorhombic crystals of silicalite having an average minimum dimension of at least about 0.2 $\mu m$.

In one embodiment of the invention, the adsorbent comprises a para-selective adsorbent and a binder, preferably a para-selective, non-acidic medium pore molecular sieve and a binder. The binder is preferably selected from the group consisting of clay, alumina, silica, titania, zirconia, silica-alumina, silica-magnesia, silica-zirconia, silica-thoria, silica-beryllia, silica-titania, silica-alumina-thoria, silica-alumina-zirconia, silica-alumina-magnesia, silica-magnesia-zirconia, and aluminum phosphate.

A para-selective adsorbent is a molecular sieve that, when subjected to an equal molar mixture of $C_8$ aromatics at 50° C., adsorbs pX and EB preferentially over mX and oX, such that the total pX and EB in the adsorbate is at least about 75% relative to the total $C_8$ aromatics.

A preferred para-selective adsorbent, when subjected to an equal molar mixture of $C_8$ aromatics at 50° C., will adsorb pX and EB preferentially over mX and oX, such that the total pX and EB in the adsorbate is greater than about 75% relative to the total $C_8$ aromatics.

A more preferred para-selective adsorbent, when subjected to an equal molar mixture of $C_8$ aromatics at 50° C., will adsorb pX and EB preferentially over mX and oX, such that the total pX and EB in the adsorbate is at least about 80% relative to the total $C_8$ aromatics, even more preferably, at least about 85% relative to the total $C_8$ aromatics, still more preferably, at least about 90% relative to the total $C_8$ aromatics; and yet more preferably, at least about 95% relative to the total $C_8$ aromatics; and most preferably, at least about 97% relative to the total $C_8$ aromatics.

In the present invention the operating temperature is preferably from about 350° F. to about 750° F. and the operating pressure is preferably from about 30 psia to about 400 psia (from about 206 kPa to about 2760 kPa).

The PSA component of the present invention additionally relates to a method to separate para-xylene and ethylbenzene from a gaseous feed mixture containing meta-xylene and ortho-xylene under substantially isothermal conditions comprising:

(a) adsorbing the mixture onto an adsorbent containing a para-selective adsorbent capable of selectively sorbing para-xylene and ethylbenzene at a temperature and pressure at which at least 0.01 grams of para-xylene and ethylbenzene may be adsorbed per gram of adsorbent;

(b) producing a first effluent stream containing a mixture of ortho-xylene and meta-xylene having no more than a total of about 25 mole percent of para-xylene and ethylbenzene based on total $C_8$ aromatics, preferably less than about 25 mole percent of para-xylene and ethylbenzene, more preferably no more than about 20 mole percent of para-xylene and ethylbenzene, more preferably less than about 20 mole percent of para-xylene and ethylbenzene, more preferably no more than about 15 mole percent of para-xylene and ethylbenzene, more preferably less than about 15 mole percent of para-xylene and ethylbenzene, more preferably no more than about 10 mole percent of para-xylene and ethylbenzene, more preferably less than about 10 mole percent of para-xylene and ethylbenzene, more preferably no more than about 5 mole percent of para-xylene and ethylbenzene, more preferably less than about 5 mole percent of para-xylene and ethylbenzene, more preferably no more than about 3 mole percent of para-xylene and ethylbenzene, more preferably less than about 3 mole percent of para-xylene and ethylbenzene, more preferably no more than about 1 mole percent of para-xylene and ethylbenzene, and most preferably less than about 1 mole percent of para-xylene and ethylbenzene based on total $C_8$ aromatics;

(c) selectively removing feed from the non-selective void volume;

(d) selectively desorbing para-xylene and ethylbenzene by decreasing partial pressure of para-xylene and ethylbenzene; and (e) collecting a stream containing para-xylene and ethylbenzene and having no more than a total of about 50 mole percent of meta-xylene and ortho-xylene based on total $C_8$ aromatics.

A practice of the invention involves principally proceeding by repeated cycles comprising in an individual cycle the above steps (a) through (e).

In a preferred embodiment of the above process, the effluent comprising meta-xylene and ortho-xylene collected in step (b) will be substantially free of ethylbenzene and para-xylene.

In a preferred embodiment of the above process, the second effluent product comprising ethylbenzene and para-xylene collected in step (e) will be substantially free of meta-xylene and ortho-xylene.

In step (a) of the process of the present invention described above, it is preferable that at least 0.01 g of para-xylene and ethylbenzene be adsorbed per gram of adsorbent; more preferable that at least 0.02 g of para-xylene and ethylbenzene be adsorbed per gram of adsorbent; still more preferable that at least 0.03 g of para-xylene and ethylbenzene be adsorbed per gram of adsorbent.

The present invention also relates to a process for separating a mixture of organic compounds having normal boiling points in a temperature range from about 800° C. to about 1600° C., which process comprises:

(a) providing an adsorbent bed comprising a para-selective adsorbent which exhibits capacity to selectively adsorb and desorb para-xylene and ethylbenzene under substantially isothermal conditions of temperature at operating pressure, disposed in a vessel having at least one inlet and at least one outlet such that gas entering an inlet passes through the adsorbent bed to an outlet, and containing a purge gas substantially free of $C_8$ aromatic compounds;

(b) flowing a gaseous feed mixture comprising xylenes and ethylbenzene into the bed through one or more of the vessel inlets, and collecting an effluent from one or more of the outlets comprising purge gas substantially free of $C_8$ aromatic compounds while selectively adsorbing para-xylene and ethylbenzene from the gaseous mixture under substantially isothermal conditions in the bed;

(c) continuing the flow of gaseous feed and collecting from one or more of the outlets and segregating a second effluent comprising m-xylene and o-xylene having no more than about 25 mole percent of p-xylene and ethylbenzene;

(d) stopping the feed mixture flowing into the bed through one or more inlets just prior to breakthrough (i.e., the adsorption front is close to the exit end of the adsorbent column), and flowing purge gas preferably in a direction counter to the direction of the $C_8$ aromatic feed, while maintaining substantially isothermal conditions in the bed, and collecting from one or more of the outlets an effluent gaseous mixture of $C_8$ aromatic feed until effluent at the outlet contains no more than about 50 mole percent of meta-xylene and ortho-xylene;

(e) continuing the flow of purge gas and collecting from one or more of the outlets and segregating an effluent comprising ethylbenzene and p-xylene which contains no more than about 50 mole percent of meta-xylene and ortho-xylene; and (f) repeating steps (b) through (e).

In a preferred embodiment of the above process, the effluent comprising m-xylene and o-xylene collected in step (c) will be substantially free of para-xylene and ethylbenzene.

In a preferred embodiment of the above process, in step (d) the effluent gaseous mixture of $C_8$ aromatic feed will be collected until the effluent at the outlet is substantially free of meta-xylene and ortho-xylene.

In a preferred embodiment of the above process, the effluent comprising ethylbenzene and p-xylene collected in step (e) will be substantially free of meta-xylene and ortho-xylene A practice of the invention involves principally proceeding by repeated cycles comprising in an individual cycle the above steps (a) through (f).

In a preferred embodiment of the process, the flow of the purge gas is counter current to the flow of the gaseous feed mixture.

In one embodiment of the process, steps (b) through (e) are repeated with a cycle time of from about 2 minutes to about 200 minutes, preferably with a cycle time of from about 3 minutes to about 50 minutes, more preferably with a cycle time of from about 3 minutes to about 30 minutes.

In an embodiment of the process at least a portion of the effluent gaseous mixture collected in step (d) is admixed with the gaseous feed mixture in subsequent cycles.

In another embodiment of the process, the purge gas comprises hydrogen, and steps (b) through (e) are repeated with a cycle time of from about 3 minutes to about 30 minutes under substantially isothermal conditions at a temperature of about 350° F. to about 750° F. and at constant operating pressure at a pressure of at least about 30 psia.

An additional embodiment of the invention comprises a process for separating a mixture of ethylbenzene and the isomers of xylene, which process comprises:

(a) providing an adsorbent bed comprising a para-selective adsorbent which exhibits capacity to selectively adsorb and desorb para-xylene and ethylbenzene under substantially isothermal conditions at operating pressure, disposed in a vessel having at least one inlet and at least one outlet such that gas entering an inlet passes through the particulate bed to an outlet and pressurizing the vessel with a mixture comprising meta-xylene and ortho-xylene to a preselected pressure for adsorption;

(b) flowing a gaseous feed mixture comprising xylene isomers and ethylbenzene into the adsorbent bed through one or more inlets and displacing the meta-xylene and ortho-xylene in the vessel while selectively adsorbing ethylbenzene and para-xylene from the gaseous feed mixture under substantially isothermal conditions in the adsorbent bed;

(c) collecting from one or more of the outlets a first effluent product comprising meta-xylene and ortho-xylene which contains no more than a total of about 25 mole percent of ethylbenzene and para-xylene while maintaining substantially isothermal conditions in the adsorbent bed and the flow of feed at the pressure for adsorption;

(d) replacing the feed mixture flowing into the bed though one or more inlets with a purge gas comprising para-xylene and ethylbenzene substantially free of meta-xylene and ortho-xylene while maintaining the pressure for adsorption and substantially isothermal conditions in the bed, and collecting from one or more of the outlets a gaseous mixture comprising feed;

(e) reducing the pressure to desorb ethylbenzene and para-xylene while maintaining substantially isothermal conditions in the bed; and (f) collecting a second effluent product comprising ethylbenzene and para-xylene which contains no more than a total of about 50 mole percent of meta-xylene and ortho-xylene.

In a preferred embodiment of the above process:

(a) the flow of said para-xylene and ethylbenzene purge gas is countercurrent to the flow of the gaseous feed mixture;

(b) the para-xylene and ethylbenzene effluent flow during depressurization is countercurrent to the flow of the gaseous feed mixture; and (c) the flow of meta-xylene and ortho-xylene to pressurize the vessel is countercurrent to the feed gas flow.

In a preferred embodiment of the above process, the effluent comprising meta-xylene and ortho-xylene collected in step (c) will be substantially free of ethylbenzene and para-xylene.

In a preferred embodiment of the above process, the second effluent product comprising ethylbenzene and para-xylene collected in step (f) will be substantially free of meta-xylene and ortho-xylene.

A further embodiment of the invention comprises a process for separating a mixture of ethylbenzene and the isomers of xylene, which process comprises:

(a) providing at least two adsorbent beds containing a para-selective adsorbent which exhibits capacity to selectively adsorb and desorb para-xylene and ethylbenzene under substantially isothermal conditions at operating pressure, disposed in sequentially connected or interconnected vessels, each having at least one inlet and at least one outlet such that gas entering an inlet passes through the particulate bed to an outlet, and pressurizing a first vessel with a mixture comprising meta-xylene and ortho-xylene to a preselected pressure for adsorption;

(b) flowing a gaseous feed mixture comprising xylene isomers and ethylbenzene into the adsorbent bed in the first vessel though one or more inlets and displacing the meta-xylene and ortho-xylene in the vessel while selectively adsorbing ethylbenzene and para-xylene from the gaseous feed mixture under substantially isothermal conditions in the adsorbent bed;

(c) collecting from one or more of the outlets a first effluent product comprising meta-xylene and ortho-xylene which contains no more than a total of about 25 mole percent of ethylbenzene and para-xylene while maintaining substantially isothermal conditions in the adsorbent bed and the flow of feed at the pressure for adsorption;

(d) stopping the flow of feed and reducing the pressure in the first vessel sufficiently to permit removal of at least a portion of the feed from non-selective voids while maintaining substantially isothermal conditions in the bed by equalizing the pressure in the first vessel with the pressure in the second vessel which is at a lower pressure;

(e) further reducing the pressure in the first vessel to desorb ethylbenzene and para-xylene while maintaining substantially isothermal conditions in the bed; and (f) collecting a second effluent product comprising ethylbenzene and para-xylene which contains no more than a total of about 50 mole percent of meta-xylene and ortho-xylene.

In a preferred embodiment of the above process, the effluent comprising meta-xylene and ortho-xylene collected in step (c) will be substantially free of ethylbenzene and para-xylene.

In a preferred embodiment of the above process, the second effluent product comprising ethylbenzene and para-xylene collected in step (f) will be substantially free of meta-xylene and ortho-xylene.

In the above process, following step (f), a purge gas comprising meta-xylene and ortho-xylene can be added to the first vessel to displace para-xylene and ethylbenzene in the non-selective voids, and an effluent comprising the para-xylene and ethylbenzene is collected.

Another embodiment of the present invention comprises a process for separating a mixture of ethylbenzene and the isomers of xylene, which process comprises:

(a) providing an adsorbent bed comprising a para-selective adsorbent which exhibits capacity to selectively adsorb and desorb para-xylene and ethylbenzene under substantially isothermal conditions at operating pressure, disposed in a vessel having at least one inlet and at least one outlet such that gas entering an inlet passes through the particulate bed to an outlet and pressurizing the vessel with a mixture of substantially meta-xylene and ortho-xylene to a preselected pressure for adsorption;

(b) flowing a gaseous feed mixture comprising xylene isomers and ethylbenzene into the adsorbent bed though one or more inlets and displacing the meta-xylene and ortho-xylene in the vessel while selectively adsorbing ethylbenzene and para-xylene from the gaseous feed mixture under substantially isothermal conditions in the adsorbent bed;

(c) collecting from one or more of the outlets a first effluent product comprising meta-xylene and ortho-xylene xylene which contains no more than a total of about 25 mole percent of ethylbenzene and para-xylene while maintaining substantially isothermal conditions in the adsorbent bed and the flow of feed at the pressure for adsorption;

(d) stopping the flow of feed and reducing operating pressure to a pressure at which para-xylene and ethylbenzene desorb while maintaining substantially isothermal conditions in the bed; and (e) collecting a second effluent product comprising ethylbenzene and para-xylene which contains no more than a total of about 50 mole percent of meta-xylene and ortho-xylene.

In the above embodiment, preferably, following step (e), a purge gas comprising meta-xylene and ortho-xylene is added to the first vessel to displace para-xylene and ethylbenzene in the non-selective voids, and an effluent comprising the para-xylene and ethylbenzene is collected.

In a preferred embodiment of the above process, the effluent comprising meta-xylene and ortho-xylene collected in step (c) will be substantially free of ethylbenzene and para-xylene.

In a preferred embodiment of the above process, the second effluent product comprising ethylbenzene and para-xylene collected in step (e) will be substantially free of meta-xylene and ortho-xylene.

In the embodiments of the pressure swing adsorption process of the present invention described above, it is preferred that the first effluent stream mixture of ortho-xylene and meta-xylene produced in the process of the invention will contain no more than about 20 mole percent of para-xylene, more preferably less than about 20 mole percent of para-xylene, more preferably no more than about 15 mole percent of para-xylene, more preferably less than about 15 mole percent of para-xylene, more preferably no more than about 10 mole percent of para-xylene, more preferably less than about 10 mole percent of para-xylene, more preferably no more than about 5 mole percent of para-xylene, more preferably less than about 5 mole percent of para-xylene, more preferably no more than about 3 mole percent of para-xylene, more preferably less than about 3 mole percent of para-xylene, and still more preferably no more than about 1 mole percent of para-xylene.

In the embodiments of the pressure swing adsorption process of the present invention described above wherein the first effluent mX/oX stream contains both para-xylene and ethylbenzene, it is preferred that the first effluent stream mixture of ortho-xylene and meta-xylene produced in the process of the invention will contain no more than about 25 mole percent of para-xylene and ethylbenzene based on total $C_8$ aromatics, preferably less than about 25 mole percent of para-xylene and ethylbenzene, more preferably no more than about 20 mole percent of para-xylene and ethylbenzene, more preferably less than about 20 mole percent of para-xylene and ethylbenzene, more preferably no more than about 15 mole percent of para-xylene and ethylbenzene, more preferably less than about 15 mole percent of para-xylene and ethylbenzene, more preferably no more than about 10 mole percent of para-xylene and ethylbenzene, more preferably less than about 10 mole percent of para-xylene and ethylbenzene, more preferably no more than about 5 mole percent of para-xylene and ethylbenzene, more preferably less than about 5 mole percent of para-xylene and ethylbenzene, more preferably no more than about 3 mole percent of para-xylene and ethylbenzene, more preferably less than about 3 mole percent of para-xylene and ethylbenzene, and still more preferably no more than about 1 mole percent of para-xylene and ethylbenzene.

In the embodiments of the pressure swing adsorption process of the present invention described above, it is preferred that the para-xylene-containing stream collected in the process of the invention will contain no more than a total of about 50 mole percent of meta-xylene and ortho-xylene based on total $C_8$ aromatics, preferably less than a total of about 50 mole percent of meta-xylene and ortho-xylene, more preferably no more than a total of about 45 mole percent of meta-xylene and ortho-xylene, preferably less than a total of about 45 mole percent of meta-xylene and ortho-xylene, more preferably no more than a total of about 40 mole percent of meta-xylene and ortho-xylene, preferably less than a total of about 40 mole percent of meta-xylene and ortho-xylene, more preferably no more than a total of about 30 mole percent of meta-xylene and ortho-xylene, preferably less than a total of about 30 mole percent of meta-xylene and ortho-xylene, preferably no more than a total of about 25 mole percent of meta-xylene and ortho-xylene; preferably less than a total of about 25 mole percent of meta-xylene and ortho-xylene; more preferably no more than a total of about 20 mole percent of meta-xylene and ortho-xylene, preferably less than a total of about 20 mole percent of meta-xylene and ortho-xylene, more preferably no more than a total of about 15 mole percent of meta-xylene and ortho-xylene, preferably less than a total of about 15 mole percent of meta-xylene and ortho-xylene, more preferably no more than a total of about 10 mole percent of meta-xylene and ortho-xylene, preferably less than a total of about 10 mole percent of meta-xylene and ortho-xylene, more preferably no more than a total of about 5 mole percent of meta-xylene and ortho-xylene, and most preferably less than a total of about 5 mole percent of meta-xylene and ortho-xylene based on total $C_8$ aromatics.

In the most preferred embodiments of the pressure swing adsorption process of the present invention, the effluent product stream containing para-xylene, or para-xylene and ethylbenzene, will be substantially free of meta-xylene and ortho-xylene, and the effluent product stream containing meta-xylene and ortho-xylene will be substantially free of para-xylene, or substantially free of para-xylene and ethylbenzene.

A purge gas substantially free of $C_8$ aromatic compounds will contain no more than about 10 wt %, and preferably less than about 5 wt %, and most preferably less than about 2 wt % of $C_8$ aromatic compounds.

A fraction or stream substantially free of p-xylene and ethylbenzene will contain no more than a total of about 5 mole percent of p-xylene and ethylbenzene based on total $C_8$ aromatics.

A fraction or stream substantially free of para-xylene will contain no more than about 5 mole percent of para-xylene based on total $C_8$ aromatics. Preferably such a fraction will contain no more than about 1 mole percent of para-xylene based on total $C_8$ aromatics.

For those process steps conducted at constant pressure, those skilled in the art will recognize that during operation there may be slight variations in pressure due to pressure drops across the system or changes in flows; however the pressure will remain substantially constant.

A fraction or stream substantially free of m-xylene and o-xylene will contain no more than a total of about 25 mole percent of m-xylene and o-xylene based on total $C_8$ aromatics. Preferably such a stream will contain no more than about 20 mole percent, more preferably no more than about 15 mole percent; still more preferably no more than about 10 mole percent; and most preferably no more than about 5 mole percent of m-xylene and o-xylene based on total $C_8$ aromatics.

The PSA component of the present invention also relates to a method of pressure swing adsorption which includes a plurality of steps and which provides recovery from a mixture comprising $C_8$ aromatics of a product stream of p-xylene or p-xylene and ethylbenzene which is substantially free of m-xylene and o-xylene as well as a product stream of meta-xylene and ortho-xylene which is substantially free of p-xylene and ethylbenzene. The PSA component of the present invention provides a pressure swing adsorption process whereby there can be obtained from a feed comprising $C_8$ aromatics a high yield of a high purity product stream of p-xylene and ethylbenzene and also a high yield of a high purity product stream of m-xylene and o-xylene.

DESCRIPTION OF THE PREFERRED EMBODIMENT(S)

Figure 1:
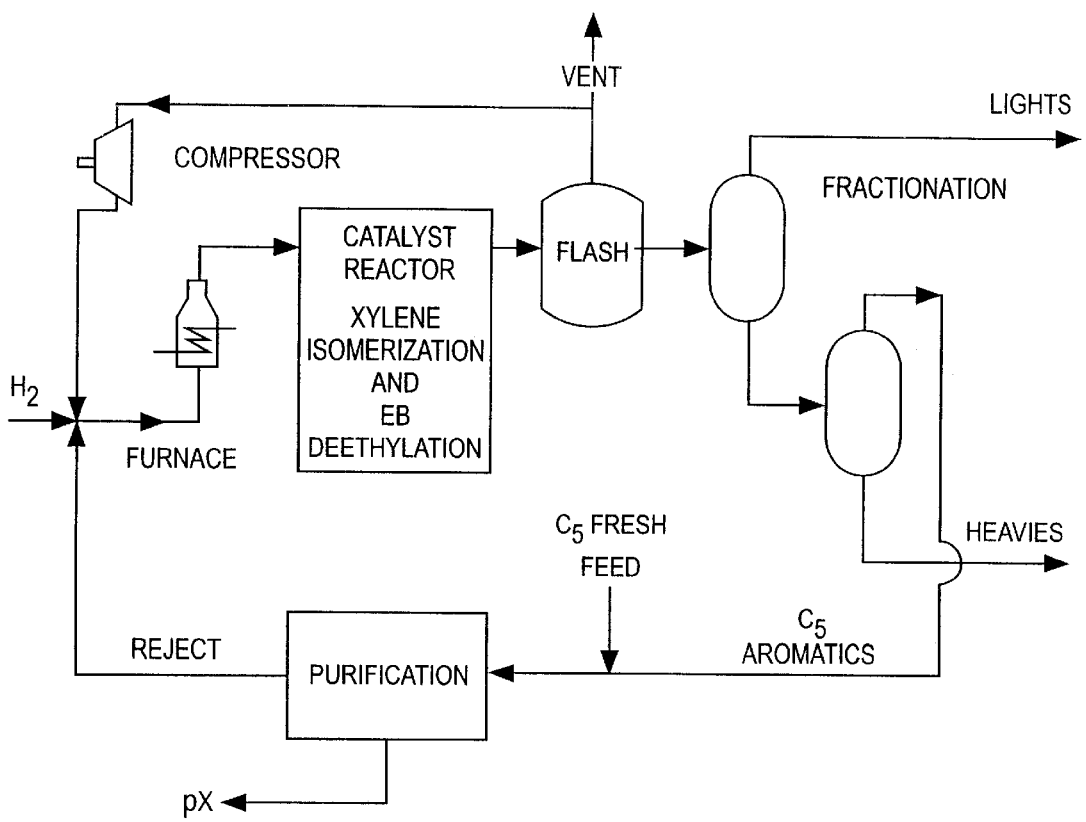
FIG. 1 is a schematic representation of the known combination of an isomerization catalyst reactor and a crystallization unit.

The present invention is a process for producing para-xylene from a toluene feed which integrates pressure swing adsorption and toluene conversion. The present invention includes a pressure swing adsorption (PSA) process component for separating para-xylene and ethylbenzene from mixed $C_8$ aromatics using a non-acidic, medium pore molecular sieve and a toluene conversion component for producing a $C_8$ aromatic feed that is then separated by means of pressure swing adsorption. Unreacted toluene is generally separated from the effluent of the toluene conversion process prior to subjecting the feed to pressure swing adsorption. Thus the process of the present invention is a toluene conversion-PSA process for producing para-xylene from toluene-containing feedstreams by converting the toluene to $C_8$ aromatics comprising xylenes and ethylbenzene which are then separated by PSA to produce a para-xylene-rich stream comprising para-xylene or para-xylene and ethylbenzene and another stream comprising meta-xylene and ortho-xylene. The para-xylene-rich stream may be purified by crystallization or simulated moving bed adsorption chromatography (SiMBAC) to produce high purity para-xylene, and the mX/oX stream may be isomerized to give a C8 aromatic stream in which the xylenes are in equilibrium which can be recycled to the PSA unit. Reject streams from PSA and/or the following purification may be subjected to isomerization and/or ethylbenzene conversion and recycled to the PSA or separation sections of the process.

When crystallization is used to purify the pX-rich stream from the PSA unit, a para-xylene-lean reject stream from the crystallization unit which comprises $C_8$ aromatics may be sent to a catalyst reactor, where the xylenes are isomerized to equilibrium and where at least a portion of any ethylbenzene in the stream is converted to products which can be separated by fractional distillation from the $C_8$ aromatics. The para-xylene-lean reject stream may be combined with the mX/oX-rich effluent stream from the PSA prior to sending it to the isomerization reactor. An additional catalyst reactor may be used to pretreat the $C_8$ aromatic feed to convert at least a portion of the ethylbenzene to xylenes or products which can be separated by fractional distillation from the C8 aromatics prior to sending the $C_8$ aromatic feedstream to the PSA unit. An additional catalyst reactor may be used to treat the para-xylene-lean reject stream from the crystallization unit to convert at least a portion of any ethylbenzene in the stream to xylenes or products which can be separated by fractional distillation from the $C_8$ aromatics prior to sending the $C_8$ aromatics to the PSA unit.

PSA Component

The PSA component of the present invention uses selective adsorption, selective desorption and displacement at substantially isothermal temperatures to provide a substantially pure product stream of para-xylene and ethylbenzene and a substantially pure stream of ortho-xylene and meta-xylene. The components in these streams can be further separated to provide substantially pure para-xylene, ethylbenzene, ortho-xylene, and meta-xylene products by methods known in the art.

In the process of the present invention the molecular sieve preferably comprises a para-selective, non-acidic medium pore molecular sieve, more preferably, silicalite. Most preferably, the molecular sieve comprises orthorhombic crystals of silicalite having an average minimum dimension of at least about 0.2 µm.

A para-selective adsorbent is an adsorbent that, when subjected to an equal molar mixture of xylenes at 122° F. (50° C.), adsorbs para-xylene preferentially over meta-xylene and ortho-xylene, such that the total para-xylene in the adsorbate is at least about 75% relative to the total $C_8$ aromatics, preferably greater than 75% relative to the total $C_8$ aromatics; more preferably, at least about 80% relative to the total $C_8$ aromatics; even more preferably, at least about 85% relative to the total $C_8$ aromatics; still more preferably, at least about 90% relative to the total $C_8$ aromatics; and yet more preferably, at least about 95% relative to the total $C_8$ aromatics; and most preferably, at least about 97% relative to the total $C_8$ aromatics.

The adsorbent used in the process of the present invention may comprise a para-selective adsorbent and a binder, preferably a para-selective, non-acidic medium pore molecular sieve and a binder. When a molecular sieve and binder are used as the adsorbent, the binder is preferably selected from the group consisting of clay, alumina, silica, titania, zirconia, silica-alumina, silica-magnesia, silica-zirconia, silica-thoria, silica-beryllia, silica-titania, silica-alumina-thoria, silica-alumina-zirconia, silica-alumina-magnesia, silica-magnesia-zirconia, and aluminum phosphate.

Preferably, the adsorbent will contain about 5 to about 100 weight percent molecular sieve.

In the process of the present invention, it is preferred that at least 0.01 grams of para-xylene is adsorbed per gram of molecular sieve, more preferable that at least 0.02 grams of para-xylene is adsorbed per gram of molecular sieve, and most preferable that at least 0.03 grams of para-xylene is adsorbed per gram of molecular sieve.

The PSA process of the present invention, is operated at a temperature and pressure sufficient to give rapid adsorption and desorption of para-xylene and/or ethylbenzene. The temperature and pressure conditions are chosen to be able to achieve rapid adsorption/desorption rates and may vary depending upon the particular adsorbent used. Suitable temperature may be selected in ranges of above about 350° F. (176° C.), preferably above about 400° F. (200° C.), and more preferably above about 450° F. (230° C.).

Suitable pressures may be selected in ranges of above about 30 psia (206 kPa), above about 50 psia (345 kPa), and above about 100 psia (2760 kPa) with pressures preferably above about 50 psia (345 kPa).

Those skilled in the art will recognize that suitable operating temperatures and pressures for achieving sufficiently rapid adsorption and desorption in the PSA process may vary. For example the temperature and pressure may be in the ranges of about 350° F. (176° C.) to about 750° F. (400° C.) and about 30 psia (206 kPa), to about 400 psia (2760 kPa); more preferably about 400° F. (200° C.) to about 650° F. (350° C.) and about 50 psia (345 kPa) to about 300 psia (2070 kPa); more preferably about 450° F. (225° C.) to about 600° F. (300° C.) and about 50 psia (345 kPa) to about 250 psia (1380 kPa).

In the PSA process of the present invention, the operating temperature is typically at least about 350° F. (176° C.), preferably at least about 400° F. (200° C.) more preferably at least about 450° F. (230° C.), more preferably at least about 500° F. (260° C.), more preferably at least about 550° F. (285° C.). For some embodiments, the temperature may be at least about 600° F. (315° C.). The operating temperature may range from about 350° F. (176° C.) to about 750° F. (400° C.) preferably from about 450° F. to about 750° F. (about 230° C. to about 400° C.); more preferably from about 500° F. to about 750° F. (about 260° C. to about 400° C.); more preferably, from about 500° F. to about 700° F. (about 260° C. to about 370° C.), more preferably about 550° F. (285° C.) to about 700° F. (370° C.)

In the process of the present invention, the operating pressure is at least about 30 psia (206 kPa), preferably at least about 50 psia (345 kPa) and may range from about 50 psia (345 kPa) to about 400 psia (2760 kPa). The operating pressure will preferably range from about 30 psia to about 400 psia, more preferably from about 50 psia to about 400 psia, more preferably from about 100 psia to about 400 psia (from about 690 kPa to about 2760 kPa), more preferably from about 150 psia to about 350 psia (from about 1715 kPa to about 2410 kPa). For some embodiments, the pressure may range from about 200 psia to about 300 psia (from about 1380 kPa to about 2070 kPa).

The term "substantially isothermal" means that the only change in temperature of the adsorbent during the PSA cycle is due to the heats of adsorption and desorption.

References to "substantially constant pressure" or "substantially constant operating pressure", mean that during the process referred to there is no depressurization of the adsorption vessel so that it remains at constant pressure; however, those skilled in the art will recognize that there may be some slight variation in pressure due to changes in flows or that the partial pressure of the adsorbed phase may be reduced by an inert purge gas.

A "substantially pure product stream of para-xylene and ethylbenzene" means a stream containing para-xylene and ethylbenzene with less than a total of 25 mole percent, and preferably less than 10 mole percent, and most preferably less than 5 mole percent meta-xylene and ortho-xylene based on total $C_8$ aromatics.

A "substantially pure product stream of ortho-xylene and meta-xylene" means a stream containing ortho-xylene and meta-xylene with less than a total of 5 mole percent, and preferably less than 1 mole percent of para-xylene and ethylbenzene based on total $C_8$ aromatics.

The present invention relates to a pressure swing adsorption process for separation of para-xylene (pX) and ethylbenzene (EB) from mixed $C_8$ aromatics using a para-selective adsorbent. For the purpose of this invention, a para-selective adsorbent is defined as a material that, when subjected to an equal molar mixture of $C_8$ aromatics at 50° C., adsorbs pX and EB preferentially over mX and oX, such that the total pX and EB in the adsorbate is at least about 75% relative to the total $C_8$ aromatics.

Preferably, a para-selective adsorbent, when subjected to an equal molar mixture of $C_8$ aromatics at 50° C., will adsorb pX and EB preferentially over mX and oX, such that the total pX and EB in the adsorbate is greater than about 75% relative to the total $C_8$ aromatics.

The preferred adsorbent is a para-selective adsorbent, preferably a para-selective non-acidic molecular sieve, more preferably a para-selective, non-acidic, medium pore molecular sieve of the MFI structure type (same structure as the acidic zeolite ZSM-5 but with the acid sites replaced with neutral moieties so that the molecular sieve is non-catalytic and does not isomerize xylenes). A particularly preferred adsorbent is silicalite. The process is operated in the vapor phase at elevated temperatures and pressures. The pX and EB are substantially adsorbed at high partial pressures while meta-xylene (mX) and ortho-xylene (oX) are not substantially adsorbed. A fixed bed of adsorbent is saturated with pX and EB, wherein the feed to the process is stopped, and then lowering the partial pressure desorbs the pX and EB. The process effluent is rich in pX and EB.

The pressure swing adsorption process is preferably a fixed-bed, batch-wise isothermal process for separation of pX and EB from mX and oX. The separation is based on the selective adsorption of pX and EB into a para-selective adsorbent, such as orthorhombic silicalite crystals having an average minimum dimension of around 0.2 $\mu$m or greater, at high pressure and desorption at low pressure. At high pressure, pX and EB are adsorbed, while mX and oX pass through the bed and are essentially not adsorbed producing a substantially pure stream of mX and oX which contains only minor amounts of other substances. The mX and oX may be collected at the outlet of the bed and recycled to an isomerization catalyst to produce more pX or a portion or all may be further separated to produce pure mX and/or pure oX. After saturation of the adsorbent the feed is discontinued and the pX and EB are desorbed by lowering the xylene partial pressure. By operating in the vapor phase at high temperatures, preferably greater than about 350° F. (176° C.) the rates of both adsorption and desorption are fast, minimizing cycle time and reducing the amount of adsorbent and capital expense required for the separation. Use of a non-acidic zeolite or molecular sieve, such as silicalite, eliminates undesirable catalytic reactions of the adsorbed EB and pX, and avoids adsorption of olefins contaminants which reduce the adsorption capacity of the adsorbent.

In the present invention a preferred adsorbent is silicalite molecular sieve, comprising orthorhombic crystals having an average minimum dimension of around 0.2 $\mu$m or greater, which has high para-xylene and ethylbenzene selectivity. The para-xylene adsorption capacity of the silicalite adsorbent is from about 1 to about 15 wt %. at saturation. Adsorbent capacity is typically defined as grams adsorbate (i.e., material adsorbed) divided by grams adsorbent and can also be expressed as a weight percent by multiplying by 100. The process is conducted in the gas phase at a temperature of from about 350° F. to about 750° F. (about 176° C. to about 400° C.) and the unit pressure is about 30 to about 400 psia (about 206 kPa to about 2760 kPa).

The present invention is a pressure swing adsorption process for separation of pX and EB from mixtures of $C_8$ aromatics using a non-acidic, para-selective adsorbent, such as silicalite molecular sieve, comprising orthorhombic crystals having an average minimum dimension of around 0.2 $\mu$m or greater. During adsorption, mX and oX are substantially not adsorbed, while pX and EB are substantially adsorbed. The process will preferably operate at about 500° F. to about 750° F. (about 260 to about 400° C.) with pX partial pressures of about 30 to about 150 psi (about 200 to about 1000 kPa), preferably about 40 to about 120 psi (about 265 to about 800 kPa). Selective adsorption of pX and EB (from a feed containing pX, EB, mX and oX) occurs with a silicalite adsorbent, comprising orthorhombic crystals having an average minimum dimension of around 0.2 $\mu$m or greater. At elevated temperatures [greater than about 350° F. (176° C.), adsorption of pX or pX/EB is effected at high partial pressures [greater than about 25 psia (about 170 kPa) partial pressure)]. Subsequently, rapid desorption without catalytic reaction is effected by lowering the partial pressure of the adsorbates. The partial pressure may be decreased by lowering the total pressure in the adsorption vessel or by purging the bed with an inert flow, for example, He, $N_2$, $H_2$, $CH_4$, $CO_2$ etc., while maintaining the unit pressure. The purge gas first displaces the $C_8$ aromatic feed from the non-selective void volume which lowers the partial pressure of para-xylene and ethylbenzene in the adsorption vessel and then sweeps out the adsorbate (substantially para-xylene and ethylbenzene) as it desorbs from the molecular sieve pores.

The present invention is a process for separation of para-xylene (pX) and ethylbenzene (EB) from meta-xylene (mX) and ortho-xylene (oX). The separation is based on selective adsorption of pX and EB into a non-acidic, silica molecular sieve, having structure type MFI (said material is commonly referred to as silicalite), comprising orthorhombic crystals having an average minimum dimension of around 0.2 $\mu$m or greater, at a higher partial pressure, followed by selective desorption (i.e., no isomerization upon desorption) at a lower partial pressure. The process is operated in a batchwise mode by first passing a stream containing a mixture of EB, pX, mX and oX over a fixed bed of silicalite. At high xylene partial pressure, pX and EB are substantially adsorbed, while mX and oX pass through the bed and are substantially not adsorbed. The mX and oX are collected at the outlet of the bed during the adsorption of pX and EB. After saturation of the silicalite, the feed is discontinued and the pX and EB are desorbed by lowering the xylene partial pressure. By operating in the vapor phase at high temperatures [greater than 450° F. (230° C.)], the rates of both adsorption and desorption are fast minimizing cycle time and reducing the amount of silicalite required for separation. Use of a non-acidic molecular sieve, such as silicalite eliminates undesirable catalytic reactions of the adsorbed EB and pX which occur with H-ZSM-5. Furthermore, non-acidic silicalite is less subject to adsorption of olefin contaminants, which reduce the adsorption capacity of H-ZSM-5.

Non-acidic molecular sieves of the MEL structure type are microporous materials having similar pore size and adsorption capacity to MFI molecular sieves, and as such would be expected to behave similarly. Both MFI and MEL molecular sieves are classified as medium pore molecular sieves. Other medium pore molecular sieves that may find use in the present invention are structure types MTW (12 ring structure, e.g., ZSM-12), ATO (12 ring structure, e.g., ALPO-31), NES (10 ring structure, e.g., Nu-87), TON (10 ring structure, e.g., Theta-1, ZSM-22), MTT (10 ring structure, e.g., ZSM-23), MFS (10 ring structure, e.g., ZSM-57), FER (10 ring structure, EUO (10 ring structure), AEL (10 ring structure, e.g., ALPO-11), AFO (10 ring structure, e.g., ALPO-41), and SUZ-4 (10 ring structure).

Large pore molecular sieves, such as mordenite, zeolite Beta, and faujasites, and amorphous adsorbents, such as silica, alumina, and clays, are non-selective, and therefore undesirable for use in the present invention, while small pore zeolites, such as zeolite A, are too small to admit pX and EB into the pores.

The adsorbent can be contained in one or more containers or vessels in which separation of a substantially pure stream of mX/oX and a substantially pure stream of pX/EB is effected using programmed flow into and out of the container or vessel. The separation of components taking place in the adsorbent column is a pressure swing adsorption separation wherein the cycle time is defined as the interval of time starting when feed is admitted into the vessel and ending at the time the vessel has been repressurized (i.e., when it is ready for the next addition of feed). Therefore, the cycle time can be described as the time interval at which feed is introduced to the pressurized adsorbent vessel, e.g., every 1 minute, every 5 minutes, every 10 minutes, every 15 minutes, etc. The "cycle" is the complete PSA process (i.e., summation of all the stages). Stages are usually discrete steps in the overall process, such as Feed, Blowdown, Purge, Repressurization; Feed Pressure Equalization, Blowdown, Purge, Repressurization; or Feed, Rinse, Blowdown, Repressurization, etc. However, in some cases the designation of stages can be more arbitrary, such as in the case of a process at constant pressure using a purge gas such as $CH_4$, $CO_2$, He, $H_2$ or $N_2$.

Effluent from the column during each cycle is separated into fractions, or cuts, which may include, for example, (1) a front end cut comprising the unadsorbed components, substantially oX and mX, (2) an intermediate cut comprising a mixture of $C_8$ aromatics where the pX content is greater than the pX content of the feed [i.e., wt % pX (intermediate) >wt % pX (feed)], and (3) a cut comprising the adsorbed components, which is substantially pure pX and EB.

The pressure swing adsorption process is carried out in the vapor phase. Preferred conditions for the process include temperatures from about 350° F. (176° C.) to about 750° F. (400° C.), preferably from about 400° F. to about 750° F. (about 205° C. to about 400° C.); more preferably from about 450° F. (230° C.) to about 750° F. (400° C.), more preferably from about 500° F. (250° C.) to about 750° F. (400° C.), more preferably, from about 600° F. (315° C.) to about 700° F. (370° C.), sufficient to maintain components in the vapor phase at system pressures from about 30 psia (206 kPa) to about 400 psia (2760 kPa), preferably from about 100 psia (690 kPa) to about 400 psia (2760 kPa), more preferably from about 150 psia (1030 kPa) to about 350 psia (2410 kPa), more preferably, from about 200 psia (1380 kPa) to about 300 psia (2070 kPa). The process is conducted at a substantially isothermal temperature.

The pressure swing adsorption (PSA) of the present invention may be conducted in staged cycles. One embodiment of the invention comprises a pressure swing adsorption cycle in which the pressure of the adsorbent vessel is substantially the same throughout the PSA cycle, and removal of the feed from the non-selective void volume and subsequent desorption of pX/EB is accomplished with a gas purge, such as methane hydrogen, nitrogen, or helium. Another embodiment of the invention comprises a four-stage PSA cycle in which a rinse stream of substantially pX/EB is used to displace feed from the non-selective void volume prior to desorption of pX/EB via lowering the absolute pressure of the adsorbent vessel.

A third embodiment of the invention comprises a four-stage PSA cycle in which pX/EB is desorbed by lowering the absolute pressure of the adsorbent vessel, and then is subsequently displaced from the non-selective void volume by a purge stream of substantially mX/oX.

A fourth embodiment of the invention comprises a PSA cycle similar to the third embodiment, with the exception that depressurization occurs in at least two steps, such that gas from depressurization is used to pressurize a regenerated bed (i.e., the cycle contains at least one pressure equalization step).

A fifth embodiment of the invention comprises a PSA cycle employing pressure equalization, a pX/EB rinse step prior to desorption of pX/EB by depressurization, and an mX/oX purge step.

In describing the preferred embodiments of the invention which are illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

Pressure Swing Adsorption Cycle for pX/EB Separation

The pressure swing adsorption process of the present invention is preferably a fixed-bed, batch-wise substantially isothermal process which can be used to separate para-xylene (pX) and ethylbenzene (EB) from meta-xylene (mX) and ortho-xylene (oX). The separation is based on molecular size and consists of the selective adsorption of the smaller $C_8$ aromatics (pX and EB) into a non-acidic, para-selective molecular sieve, such as silicalite, comprising orthorhombic crystals having an average minimum dimension of about 0.2 $\mu$m or greater, while mX and oX pass through the bed and are not adsorbed. The key to a viable commercial process (fast cycles, minimal adsorbent and capital) is operating at a temperature where the desorption rate is high, and consequently, at a pressure giving sufficient adsorption at that temperature. Thus, in the process of the invention, adsorption occurs at high pressure and high temperature; whereas, desorption occurs at low pressure and high temperature. The mX/oX stream may be recycled to the isomerization catalyst producing more pX or it may be further separated to obtain mX and/or oX. The pX/EB stream (rich in pX) may be purified via crystallization or simulated moving bed adsorption to give pX having a purity of 99% or greater. Process Specifics:

Temperature Range:

The temperature range of the PSA process used in the invention is preferably from about 350° F. to about 750° F. (about 176° C. to about 400° C.), preferably from about 400° F. to about 750° F. (about 205° C. to about 400° C.); more preferably from about 450° F. to about 750° F. (about 230° C. to about 400° C.); more preferably from about 500° F. to about 750° F. (about 260° C. to about 400° C.); more preferably, from about 500° F. to about 700° F. (about 260° C. to about 370° C.), more preferably about 550° F. (285° C.) to about 700° F. (about (285° C. to about 370° C.).

The pressure swing adsorption cycle is preferably conducted under substantially isothermal conditions in which the only change in temperature of the adsorbent during the PSA cycle is due to the heats of adsorption and desorption.

High Pressure Side: About 30 to about 420 psia.

Pressure Ratio (High Pressure/Low Pressure): 2–30.

Adsorbent Capacity: About 1 to about 15 wt % at saturation.

The adsorbent may maintain adsorption capacity through many cycles which reduces the need to replace or recondition the adsorbent. This is another cost saving advantage of the process of the present invention.

PSA Process Cycle Designs

In the descriptions that follow pX/EB comprises para-xylene and ethylbenzene and represents the adsorbed phase, which is principally pX and EB, but could also contain other adsorbable components such as benzene, toluene, 1,4-methylethylbenzene, 1,4-diethylbenzene, linear paraffins (typically $C_9$) and mono-methylbranched paraffins (also typically $C_9$). Likewise, mX/oX comprises meta-xylene and ortho-xylene and represents the non-adsorbed phase which is principally mX and oX, but could also contain other non-adsorbable components such as trimethylbenzenes, other isomers of methylethylbenzene and diethylbenzene, cycloparaffins (typically $C_9$) and other sterically bulky components in the feed.

For each embodiment, one complete cycle is described. It is to be understood that practice of the invention involves principally proceeding by repeated said cycles. In the descriptions of the embodiments of the invention, the molecular sieve adsorbent may be referred to as a zeolite; however, it is to be understood that any suitable non-acidic, medium pore molecular sieve may be used as the adsorbent.

The preferred embodiments of the PSA process are described below.

PSA Embodiment 1: Desorption with Inert Gas Purge, e.g., $CH_4$, $CO_2$, $H_2$, $N_2$, He (FIG. 4)

Figure 4:
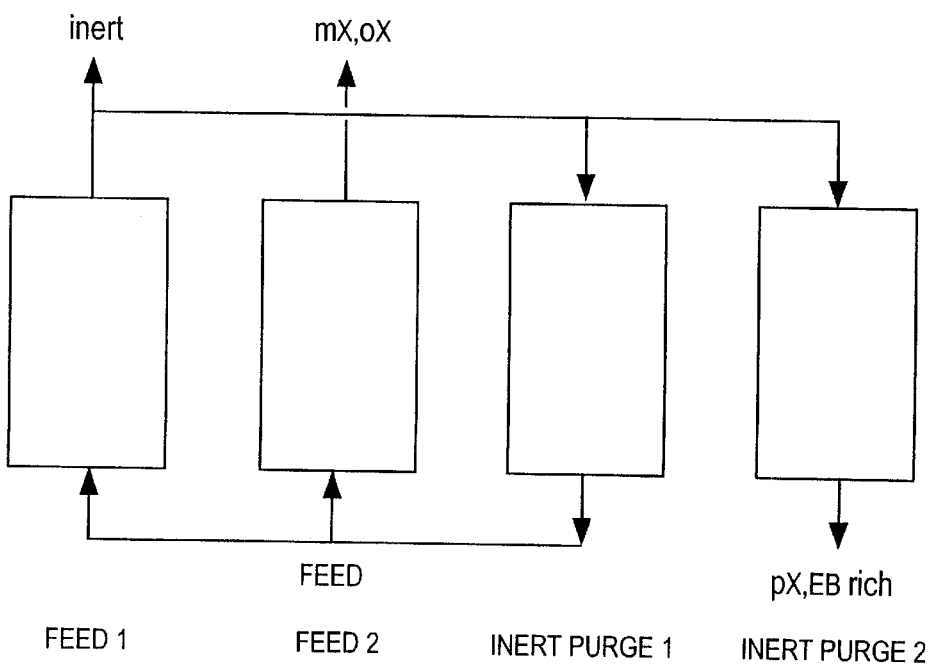
FIG. 4 is a schematic representing an adsorption cycle for pX/EB separation which operates at substantially constant system pressure and uses an inert gas purge, such as, for example, $CH_4$, $CO_2H_2$, $N_2$, or He, to accomplish desorption.

This embodiment is illustrated in FIG. 4. A typical bed of molecular sieve adsorbent contains about 20–30% of its volume in molecular sieve pores which selectively adsorb pX and EB and 80–70% of void space and large non-selective pores. This embodiment comprises a gas-phase process wherein the temperature is substantially isothermal and the total pressure is substantially constant. The pressure and temperature are selected to allow for rapid adsorption and desorption leading to rapid loading and unloading of the adsorbent bed. Cycle times may be from about 1 to about 30 minutes and are preferably no more than about 25 minutes, more preferably no more than about 20 minutes, still more preferably about 5 to about 15 minutes and most preferably, about 3 to about 15 minutes. Thus a preferred cycle time might be 3, 4, 5, 6, 7, 8, 9, 10, 11, 12, 13, 14, or, 15 minutes. Shorter cycle times are preferred since they reduce the amount of adsorbent and capital required.

Stage 1: Adsorption 1-Displacement of Purge Gas from the Void Space and Initial Adsorption of pX and EB Prior to admitting $C_8$ aromatic feed flow into the adsorbent vessel, the bed is essentially free of $C_8$ aromatics and contains the purge gas. Feed containing a mixture of substantially $C_8$ aromatics (mX, oX, pX, EB), which can also contain some paraffins and naphthenes, $C_9$+ aromatics, benzene and toluene, is passed into the adsorption vessel where pX and EB are adsorbed into the pores of the molecular sieve leaving mX and oX in the void space. As the feed flow continues into the vessel, purge gas is displaced at the outlet of the reactor and recycled to the process.

This stage continues until the purge gas is essentially displaced from the void fraction. (Purge gas may remain in a portion of the molecular sieve pores.) Just prior to hydrocarbon breakthrough, purge gas recovery is discontinued.

Stage 2: Adsorption 2 (Product Collection of mX and oX and Saturation of the Molecular Sieve Pores with PX and EB)

With the removal of purge gas from the void volume, mX and oX exit from the outlet of the adsorption bed as the feed continues to enter the adsorption bed. This mX/oX effluent stream which is substantially free of pX and EB may be collected as one of the product streams for further purification of mX and oX or may be sent to a catalyst reactor for isomerization to an equilibrium xylene mixture.

Throughout this stage pX and EB continue to adsorb into the molecular sieve and mX and oX are displaced from the void fraction by incoming feed. At the end of the stage the void fraction contains feed and the molecular sieve pores contains pX and EB. Collection of the mX and oX is discontinued just prior to breakthrough of the feed.

Stage 3: (Desorption of the Feed from the Void Fraction)

During the two desorption steps, feed is discontinued and purge gas flows in to the adsorption vessel, typically countercurrent to the flow of $C_8$ aromatics during the feed step. Because the pX and EB are more strongly adsorbed inside the pores of the molecular sieve than the feed in the void fraction, the feed is more readily displaced by the purge gas. As purge gas enters the reactor the feed in the void fraction is removed at the reactor outlet along with a small amount of pX and EB displaced from the molecular sieve. The feed from this stage may be mixed with make-up feed or sent directly to another vessel which is in one of the adsorption stages. Stage 3 is complete when essentially all of the mX and oX have been purged from the vessel.

Stage 4: Collection of pX and EB

Once the feed is displaced from the void fraction, the effluent is highly concentrated in pX and EB. Since the purge gas lowers the partial pressure of pX and EB in the adsorbent vessel, pX and EB continue to desorb from the molecular sieve and exit the adsorbent vessel. This stream is collected for further purification of pX and EB. At the end of this stage the void fraction and molecular sieve pores are essentially filled with purge gas and the system is ready to admit feed flow and begin Stage 1 again.

Figure 3:
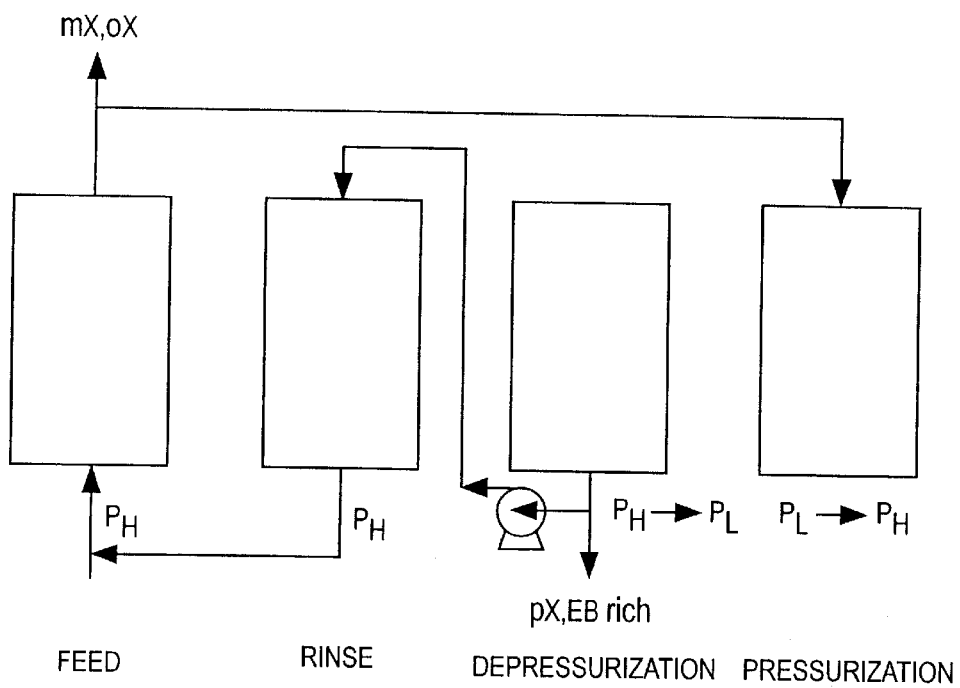
FIG. 3 is a schematic representing a four-stage pressure swing adsorption cycle for pX/EB separation in which a rinse stream of substantially pX/EB is used to displace feed from the non-selective void volume, prior to desorption via lowering of the absolute pressure.

PSA Embodiment 2: pX/EB Rinse Prior to Desorption by Depressurization (FIG. 3)

This process flow is similar to the process embodiment described above except that no $H_2$ (or $CH_4$, $CO_2$He, $N_2$, etc.) is used during the desorption stages. Rather, removal of the feed from the void fraction is accomplished by rinsing with a stream of substantially pX/EB, and then pX/EB is desorbed from the adsorbent and recovered by depressurizing the adsorption vessel. Again this is a substantially isothermal, gas-phase process with cycle times of about 3 to about 15 min.

Stage 1: Adsorption of pX and EB

Prior to the introduction of $C_8$ aromatic feed, the molecular sieve pore volume is essentially free of pX/EB and the non-selective void volume (i.e., large meso-pores in the adsorbent, interstitial space between adsorbent particles, void space in the adsorbent vessel) is filled with substantially mX/oX. A feed containing substantially $C_8$ aromatics (mX, oX, pX, EB, which can also contain some paraffins and naphthenes, $C_9$+ aromatics, benzene and toluene) then enters the adsorbent vessel and pX/EB begins to adsorb into the molecular sieve pores, and mX/oX in the feed begins to displace the mX/oX that was already in the void volume. The adsorption of pX/EB into the molecular sieve produces a heat front which can be monitored. By the time the pX/EB adsorption front reaches the end of the bed, most of the mX/oX in the void volume has been displaced and replaced with feed (mX, oX, pX, EB). This is the end of the first stage and introduction of feed is stopped just prior to breakthrough.

Stage 2: Displacement of the Feed from the Non-selective Void Volume

At the end of the first stage, the molecular sieve pores are filled with pX/EB and the non-selective void volume is filled with feed. In order to increase the recovery and purity of pX/EB during the depressurization step, the feed is displaced from the non-selective void space by the addition of a high pressure stream containing substantially pX/EB flowing countercurrent to the C8 aromatic flow during the feed step. The feed displaced during this stage may be sent to another adsorption vessel in Stage 1 of the cycle. Once the feed has been displaced and the non-selective void volume filled with pX/EB, the addition of pX/EB is stopped just prior to pX/EB breakthrough and Stage 2 is complete.

Stage 3: Collection of pX and EB

Once the feed is displaced from the void fraction, the vessel pressure is lowered resulting in desorption of the pX, EB from the molecular sieve. Effluent flow out of the adsorbent bed is typically countercurrent to the $C_8$ aromatic flow, and low pressure pX, EB is collected at the outlet of the adsorption bed for further purification. At the end of this stage the non-selective void volume and molecular sieve pores are filled with a residual amount of pX/EB and the system is ready for repressurization. Prior to repressurization, a low pressure countercurrent flow of mX/oX may be used to displace the remaining pX/EB out of the adsorption vessel.

Stage 4: Repressurization of the Adsorption Vessel

The final step in the cycle is repressurization. Typically, a high pressure stream of mX/oX flowing countercurrent to the $C_8$ aromatic flow during the feed step is used to repressurize the adsorption vessel. Following repressurization, the non-selective void space contains mX/oX and the molecular sieve pores have a residual amount of pX/EB. The system is now ready to admit feed again (Stage 1).

Figure 5:
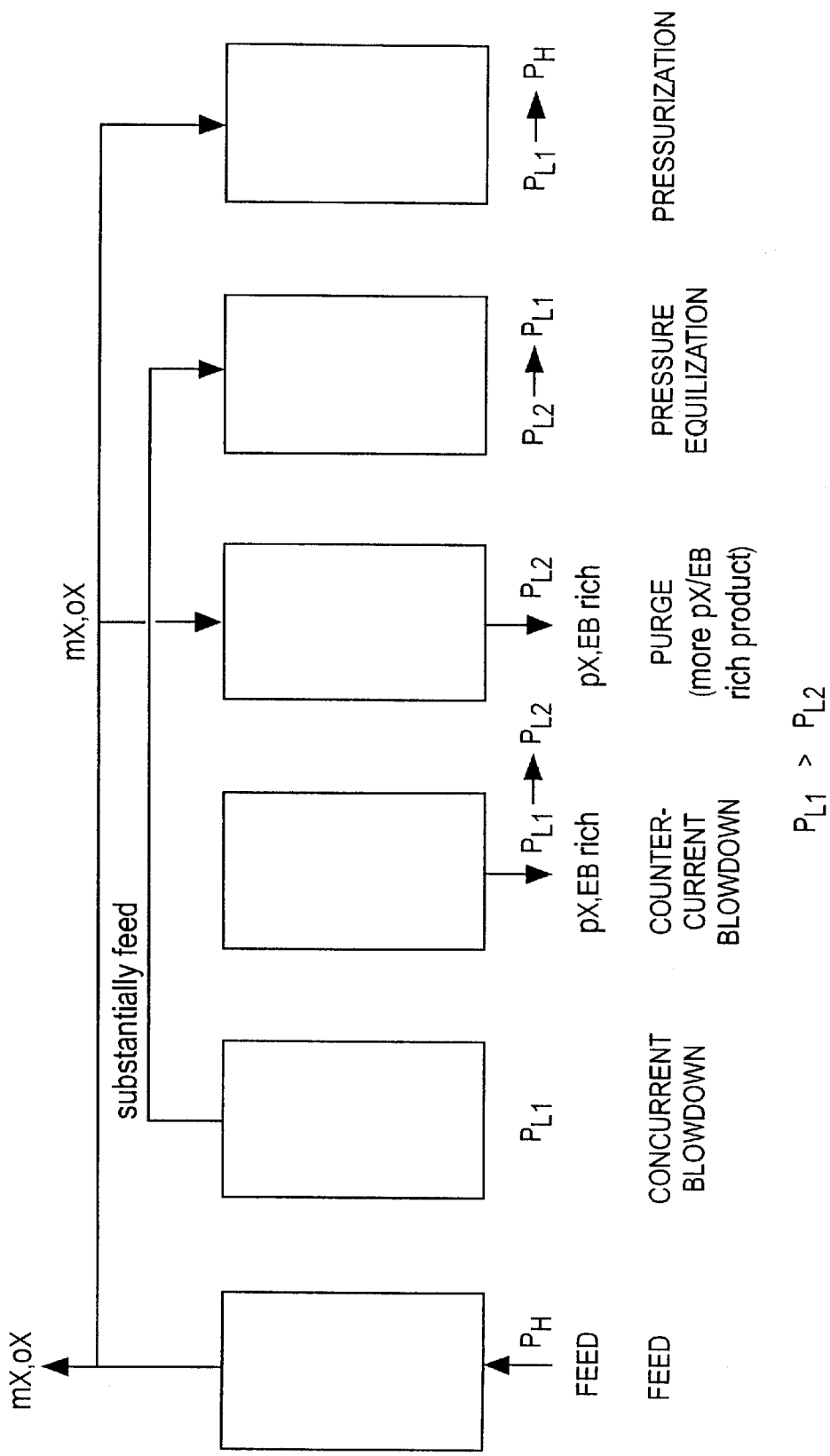
FIG. 5 illustrates a pressure swing adsorption cycle for px/EB separation similar to that described by FIG. 2, with the exception that depressurization occurs in two steps, such that the gas from the first depressurization is used to pressurize a regenerated bed (i.e., pressure equalization).

PSA Embodiment 3: Pressure Equalization Prior to pX/EB Product Collection (FIG. 5)

This embodiment of the invention comprises a five-stage PSA cycle in which pX/EB is desorbed by lowering the absolute pressure of the adsorbent vessel in at least two steps, and then subsequently displaced from the non-selective void volume by a purge stream of substantially mX/oX.

Stage 1: Adsorption of DX and EB

In the first stage, the molecular sieve pore volume is essentially free of pX/EB and the non-selective voids (i.e., large meso-pores in the adsorbent, interstitial space between adsorbent particles, and void space in the adsorbent vessel) are filled with substantially mX/oX. A feed containing substantially $C_8$ aromatics (mX, oX, pX, EB, which may also contain some paraffins and naphthenes, $C_9$+ aromatics, benzene and toluene) then enters the adsorbent vessel and pX/EB begins to adsorb into the molecular sieve pores, and mX/oX in the feed begins to displace the mX/oX that was already in the void volume. The adsorption of pX/EB into the molecular sieve produces a heat front which can be monitored. By the time the pX/EB adsorption front reaches the end of the bed, most of the mX/oX in the void volume has been displaced and replaced with feed (mX, oX, pX, EB). This displaced mX/oX effluent stream which is substantially free of pX and EB is collected as one of the product streams for further purification of mX and oX or may be sent to a catalyst reactor for isomerization to an equilibrium xylene mixture. Introduction of feed is stopped just prior to breakthrough, and this completes Stage 1.

Stage 2: Pressure Equalization

In order to increase the purity of the pX/EB product stream collected in the subsequent stage and to conserve mechanical energy, an initial pressure reduction in the vessel takes place. The vessel is depressurized to a lower pressure ($P_{L1}$) by cocurrent blowdown and equalizing of pressure with another adsorbent bed at a lower pressure ($P_{L2}$). During this step, the feed in the non-selective void volume degasses first, resulting in a higher concentration of pX/EB in the adsorbent vessel. The second absorbent vessel is pressurized with the degassing material such that its pressure increases (from $P_{L2}$ to $P_{L1}$), such that at the end of this stage the pressure in the two vessels is equalized at $P_{L1}$).

Stage 3: Recovery of the pX/EB Stream

Following pressure equalization, the adsorbent vessel is further depressurized (e.g., via countercurrent blowdown). The purity of the exiting stream increases in pX/EB during the blowdown process, such that a stream containing substantially pX/EB (based on total $C_8$ aromatics) can be obtained. At the end of Stage 3, the non-selective void volume contains substantially pX/EB and the pressure in the vessel is $P_{L2}$.

Stage 4: Removal of pX/EB in the Non-selective Void Space

Additional pX/EB can be collected from the adsorbent vessel by displacing the pX/EB in the non-selective void space. This is typically done using a stream of substantially mX/oX, although feed can also be used. At the end of Stage 4, most of the pX/EB has been removed from the non-selective void volume and replaced with mX/oX. The pressure remains at $P_{L2}$. An adsorbent vessel in this state is used for the second adsorbent vessel in the pressure equalization step (Stage 2), such that the pressure increases from $P_{L2}$ to $P_{L1}$.

Stage 5: Repressurization to PH

The final step in the cycle is to repressure the vessel from $P_{L1}$ to $P_H$ using a stream of substantially mX/oX typically flowing countercurrently to the flow during the feed stage. Thus, at the end of the cycle, the molecular sieve pore volume is essentially free of pX/EB and the non-selective void volume contains mX/oX. The vessel is now ready to begin the cycle again (i.e., Stage 1: adsorption of pX/EB from the feed.)

Figure 2:
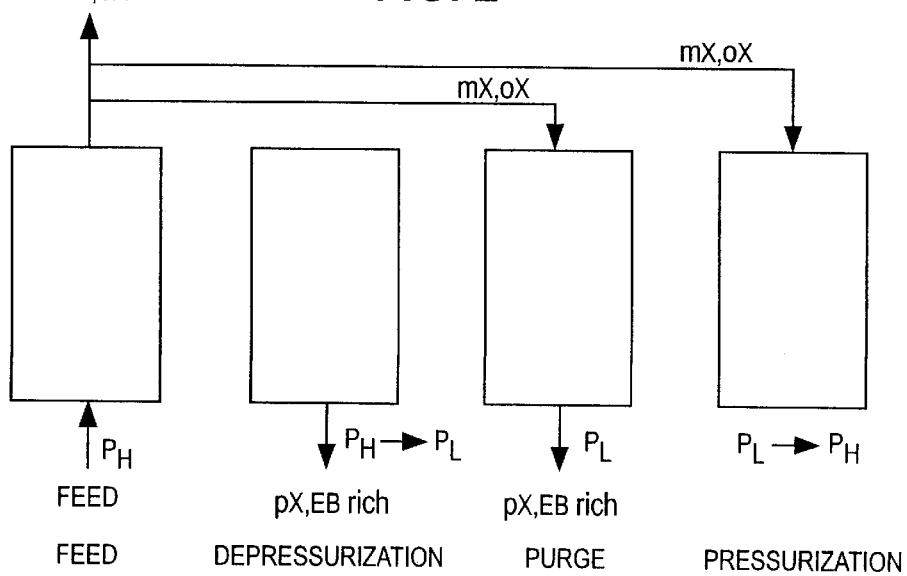
FIG. 2 is a schematic representing a four-stage pressure swing adsorption cycle for pX/EB separation in which pX/EB is desorbed by lowering the absolute pressure, and then subsequently displaced by a purge stream of substantially mX/oX.

PSA Embodiment 4: Simple 4-Stage Cycle with Purge (FIG. 2) This cycle (shown in FIG. 2) is basically the same as Embodiment 3, except depressurization occurs in one step with no pressure equalization.

PSA Embodiment 5: Pressure Equalization Prior to Rinse

This cycle is basically the same as Embodiment 3 except prior to the countercurrent blowdown step, a pX/EB rinse is used to displace the mX/oX-rich material in the void space.

Toluene Conversion Component

There are essentially two widely practiced, catalytic processes for the production of para-xylene (PX) from toluene. The first involves the conversion of toluene to mixed xylenes by either disproportionation, alkylation, or other related chemistry, followed by separation and purification of the PX. This will be broadly classified herein as a "conventional toluene process." The second class of toluene-based processes also involves the conversion of toluene, except with a catalyst that has been designed to selectively produce PX. Subsequent separation and purification of the PX is generally similar to that of conventional toluene processes, however, with appropriate modifications to better accommodate the elevated PX content of the product generated by the selective catalyst. This latter type of process will be broadly classified herein as a "selective toluene process." Examples of various toluene based processes include those disclosed in patents WO 00/69796; and WO 93/17987 incorporated herein by reference in their entireties.

The above broad categories may include the following types of toluene conversion processes:

1) toluene disproportionation processes
2) toluene alkylation (e.g. with methanol)
3) toluene alkylation with in-situ production of alkylating agent
4) transalkylation with C9 & heavier aromatics The two broad categories described above as (1) "conventional toluene process and (2) "selective toluene process" attempt to distinguish between toluene processes/catalysts that make mixed xylenes (MX, OX, PX) and those that make only PX, irrespective of which of the above reactions were used.

As taught in WO 93/17987, toluene disproportionation may be carried out in a fixed-bed reactor using 2 grams of a silica bound HZSM-5 catalyst having a silica/alumina ratio of 26, a crystal size of 0.1 micron, an Alpha Value of 731. The feed to the reactor was toluene containing 1% silicone compound having a phenylmethyl silicone to dimethyl silicone ratio of 1:1. Operating conditions are 4.0 WHSV, 480° C., 3550 kPa (500 psig), and a hydrogen/hydrocarbon ratio of 2.

Operating conditions for above the toluene disproportionation process generally include a temperature of 350–540°

C., preferably greater than 400° C., a pressure of 100 to 35000 kPa (atmospheric to 5000 psig), preferably 800 to 7000 kPa (100 to 1000 psig), a WHSV of 0.1–20, preferably 2–4, and a hydrogen to hydrocarbon mole ratio of 0.1–20, preferably 2–4. This process may be conducted in either fixed- or fluid-bed mode with attendant benefits of either operation readily obtainable.

The effluent is separated and distilled to remove the desired product, i.e., para-xylene, plus other by-products. The unreacted reactant, i.e. toluene, is preferably recycled for further reaction. The benzene is a valuable co-product.

In a preferred embodiment, the catalyst may be further modified in order to reduce the amount of undesirable by-products, particularly ethylbenzene.

Those skilled in the art will recognize that other toluene conversion processes known in the art are also suitable for use in the toluene conversion component of the present invention.

The separation and purification process component used in connection with the above toluene conversion processes also generally fall into two categories: crystallization or liquid-phase, adsorption chromatography (SiMBAC). The former was initially developed by Amoco with subsequent improvements, modifications, or incorporations by others. See, for example, the following patents: U.S. Pat. Nos. 5,329,060; 5,448,005; 5,866,740; 6,111,161; 6,114,592; 6,147,272; and WO 96/22262 (all of which are incorporated herein by reference in their entireties). Liquid-phase adsorption chromatography, also referred to as simulated moving bed adsorption chromatography (SiMBAC), is commercially licensed by UOP and IFP. SiMBAC processes are disclosed in U.S. Pat. Nos. 2,985,589; 3,201,491; 3,626,020; 3,696,107; 3,729,523; 4,039,599; 4,184,943; 4,381,419; 4,402,832 all of which are incorporated herein by reference in their entireties. It is widely recognized that, next to the feedstock costs, the separation and purification portions comprise the most expensive component of the PX production process.

The present invention comprises a process for the production of PX from a feedstream comprising toluene which uses a pressure-swing adsorption (PSA) process, in combination with toluene conversion processes for the production of PX. A primary advantage provided by the process of the present invention is that both of the crystallization and SiMBAC purification processes which have been used to separate and purify PX from a C8 aromatic stream produced by toluene conversion are most efficiently operated when used to purify a concentrated stream of PX. The PSA technology can perform a bulk separation of a para-xylene-containing effluent stream from a toluene conversion unit to further concentrate the para-xylene-containing stream and produce a para-xylene-rich stream before, optionally, sending the para-xylene-rich stream to crystallization or SiMBAC for additional purification. With the process of the present invention, portions of the various separation processes can be redesigned to decrease both capital and operating costs. In addition, the overall yield of PX will be improved by using the PSA technology.

The para-xylene/ethylbenzene stream produced in the PSA component of the present invention can be subjected to simulated moving bed adsorption to produce higher yields of para-xylene product at lower capital and energy cost.

When SiMBAC is used for separation or purification, suitable temperature and pressure operating ranges for the simulated moving bed adsorption are those that favor liquid phase. The adsorbents are generally Y zeolite ion exchanged with K or Ba ions. The operating conditions are generally atmospheric pressure and below about 30 psia. The temperature is below the boiling point, i.e., liquid phase, typically around 150° C. or less for xylenes; however, for some compositions the temperature may be up to about 200° C.

Descriptions of SiMBAC processes and process conditions which would be suitable for use for separation or purification of para-xylene-containing streams in the process of the present invention are disclosed in U.S. Pat. Nos. 2,985,589; 3,201,491; 3,626,020; 3,696,107; 3,729,523; 4,039,599; 4,184,943; 4,381,419; 4,402,832, and 5,284,992, all of which are incorporated herein by reference in their entireties.). It is widely recognized that, next to the feedstock costs, the separation and purification portions comprise the most expensive component of the para-xylene production process. The present invention has the advantage of reducing such costs and providing a more efficient process for the production of para-xylene by virtue of using PSA to significantly reduce the amount of meta-xylene and ortho-xylene sent to a simulated moving bed liquid chromatographic section or a crystallization section. In the discussion of the PSA component of the present invention herein, the amounts of meta-xylene and ortho-xylene in the para-xylene or para-xylene and ethylbenzene effluent streams are reported as mole percent based on total $C_8$ aromatics. The amount of para-xylene or para-xylene and ethylbenzene in the meta-xylene and ortho-xylene effluent streams are also reported as mole percent based on total $C_8$ aromatics. Those skilled in the art will recognize that, with regard to the concentration of pX, mX, oX, and/or EB in a given stream of pX, mX, oX, and/or EB, mole percent equals weight percent.

The pressure swing adsorption component of the process of the invention uses selective adsorption, selective desorption and displacement at substantially isothermal temperatures to provide an effluent stream of para-xylene and ethylbenzene having no more than a total of about 50 mole percent of meta-xylene and ortho-xylene based on total $C_8$ aromatics and which is preferably substantially pure, and an effluent stream of ortho-xylene and meta-xylene having no more than a total of about 25 mole percent of para-xylene and ethylbenzene based on total $C_8$ aromatics and which is preferably substantially pure. High purity para-xylene may be recovered from the para-xylene/ethylbenzene effluent stream from the PSA process by crystallization or simulated moving bed adsorption (SiMBAC).

The crystallization process used to purify the pX/EB effluent from PSA includes conventional crystallization processes known to those of skill in the art as well as the crystallization processes illustrated in U.S. Provisional Application No. 60/289,313 incorporated herein by reference.

Also suitable for use as the crystallization process are the crystallization processes disclosed in U.S. Provisional Application No. 60/289,313 incorporated herein by reference. The SIMBAC component of the invention includes conventional SiMBAC processes as well as those disclosed herein.

The components in the meta-xylene/ortho-xylene stream can be further separated to provide high purity, ortho-xylene and meta-xylene products by methods known in the art. The ethylbenzene can also be recovered in highly pure form by methods known in the art.

An embodiment of the present invention relates to converting a toluene feed to mixed C8 aromatics and then separating the toluene conversion effluent by a process comprising the use of pressure swing adsorption for separation of para-xylene (pX) and ethylbenzene (EB) from mixed $C_8$ aromatics using a para-selective adsorbent, optionally followed by crystallization or SiMBAC of the para-xylene to produce product grade para-xylene of high purity. A high purity para-xylene product will have a purity of at least about 99.5 wt %, more preferably at least about 99.7 wt %, still more preferably at least about 99.8 wt %, and most preferably at least about 99.9 wt %. The process of the invention further includes separation of meta-xylene and ortho-xylene as part of the above PSA process and isomerizing the meta-xylene and ortho-xylene to give an equilibrium mixture of meta-xylene, ortho-xylene, and para-xylene.

The PSA process may be integrated with crystallization to produce high purity para-xylene. Any of the known crystallization methods may be integrated with the PSA process of the invention to give a high purity para-xylene product having a purity of at least about 99.5 wt %.

Examples of crystallization processes which could be used as the crystallization component of the PSA-crystallization process of the present invention are disclosed in U.S. Pat. Nos. 2,985,694; 3,729,523; 5,284,992, 5,329,060; 5,448,055, 3,177,265, 3,467,724, 3,662,013, 5,992,924, 6,111,1611, and 6,147,272 all of which are incorporated herein by reference in their entireties.

Crystallization may be conducted in several crystallization stages by passing a para-xylene-containing mixture into a crystallizer operated at a temperature sufficient to induce crystallization of para-xylene, typically from about 0° F. to about −80° F.(about −18° C. to about −62° F., removing the mixture from the crystallizer, separating the para-xylene and passing the mother liquor to a second stage for further cooling and the recovery of additional para-xylene. The resulting mother liquor may then be sent to a distillation stage to recover and ethylbenzene in the mixture. Stages crystallization using a series of crystallizers usually provides optimum results. Typically, in a continuous process the bottoms from the distillation are continuously recycled to the crystallization stage for the recovery of additional para-xylene.

In a two-stage crystallization, the first stage may use several crystallizers in series. The first crystallizer stage should be at a temperature which allows para-xylene crystals to form with out crystallizing other components in the mixture, typically this may be about −50° C. to about −70° C. (−58° F. to about −94° F.). Effluent from the crystallizer is separated into para-xylene crystals and mother liquor. Typically, at least a portion of the mother liquor is recycled to an isomerization unit and isomerized to produce an equilibrium mixture of xylenes. The crystallized para-xylene from the first stage can be melted and sent to a second crystallization stage wherein the operating conditions are similar to that of the first crystallization stage with the exception that the crystallization temperature is higher, typically about −10° C. (about 14° F.). The para-xylene crystals from the second stage typically have a higher purity that those from the first crystallization stage. The crystalline para-xylene from the second crystallization may be treated further to increase the para-xylene purity by washing it with high purity para-xylene product to remove adhering second stage mother liquor. Other solvents, such as toluene, n-pentane, and aqueous alcohols may be used as the wash liquid; however, they have the disadvantage of requiring an additional distillation step to remove the wash solvent from the para-xylene product.

The PSA process can produce effluent streams having a para-xylene concentration of at least about 40 wt %, more preferably at least about 45 wt %, more preferably at least about 50 wt %, more preferably at least about 55 wt %, more preferably at least about 60 wt %, more preferably at least about 65 wt %, more preferably at least about 70 wt %, more preferably at least about 75 wt %, more preferably at least about 80 wt %, more preferably at least about 85 wt %, more preferably at least about 90 wt %, more preferably at least about 95 wt %, and more preferably at least about 97 wt % which can be fed to a crystallization unit to produce high purity para-xylene.

Crystallization processes which take advantage of the ability of the PSA process to produce effluent streams of $C_8$ aromatics having enriched para-xylene concentrations are particularly suitable for integration with the PSA process.

As stated above, crystallization processes are known for isolating a concentrate of crystalline para-xylene from a para-xylene-containing stream such as that produced in the PSA component of the present invention. One such process comprises cooling the mixture until para-xylene crystallizes from the mixture. The crystallization of para-xylene from such mixtures typically requires temperatures as low as −100° F. to maximize the recovery of para-xylene. However, the exact temperature will depend on the composition of the mixture of xylenes. Processes for crystallizing para-xylene from such mixtures are described, for example, in U.S. Pat. Nos. 2,866,833 and 3,177,265, incorporated herein by reference in their entireties. In these processes one or more crystallizers, such as a scraped wall crystallizer, are used, each at progressively lower temperatures. For example, the first crystallizer may operate at a temperature of −50° F. to about −60° F., the second at about −65° F. to about −80° F., and the third at about −85° F. to about −95° F. The mixture exiting the final crystallizer is a mixture of mother liquor and solid enriched in crystalline para-xylene. The mother liquor is enriched in ortho- and meta-xylene. The mixture exiting the last crystallizer is separated in a suitable separation apparatus operated at a temperature sufficiently low to maintain the crystalline para-xylene in the crystalline state. Solid para-xylene, i.e., the cake, isolated from the separation apparatus is typically about 80 to about 95 weight percent para-xylene. The impurities are due to the mother liquor adhering to the para-xylene crystals and/or due to impurities contained within the crystal structure of the crystalline para-xylene. When the purity of crystalline para-xylene is referred to in describing this crystallization process, it accounts for impurities adhering to the outside of the crystals and/or impurities contained within the para-xylene crystals. Such impure crystalline para-xylene can be used to prepare pure crystalline para-xylene.

Since the mother liquor separated from the crystalline para-xylene is enriched in meta-xylene and ortho-xylene, it is advantageous to direct it to a xylene isomerization unit wherein a mixture of xylenes having a less than equilibrium amount of para-xylene is contacted with a suitable catalyst to isomerize the xylenes to a mixture containing an equilibrium mixture of the xylenes. Processes for isomerizing a mixture of xylenes containing less than an equilibrium amount of para-xylene to an equilibrium mixture are disclosed, for example, in U.S. Pat. No. 4,269,813.

A slurry process can be used to obtain very pure para-xylene from impure crystalline para-xylene. Impure crystalline para-xylene having a purity of less than about 99.7 weight percent, for example, para-xylene having a purity of about 80 to less than about 99.7 weight percent, can be purified to crystalline para-xylene having a purity of at least about 99.7 weight percent, preferably at least about 99.8 weight percent, and most preferably at least about 99.85 weight percent para-xylene, by contacting the impure crystalline para-xylene in the form of a slurry with a liquid containing para-xylene at a temperature of at least 32° F., preferably about 35° F. to about 45° F., more preferably at a temperature of about 37° F. to about 44° F., and most preferably at a temperature of about 39° F. to about 42° F., for a time sufficient to increase the purity of the crystalline para-xylene to at least about 99.7 weight percent, more preferably at least about 99.8 weight percent, and most preferably at least about 99.85 weight percent para-xylene. It is necessary to use these temperatures for the slurry in order to obtain the desired very high purity para-xylene. When operated as a continuous process, the residence time of the slurry of crystalline para-xylene and liquid para-xylene in the vessel used for containing the slurry is suitably about 0.2 to about 2 hours, more preferably about 0.25 to about 0.5 hour. The amount of liquid in the slurry should be an amount to produce a mixture that can be slurried and pumped. For example, the slurry can be about 30 to about 60 weight percent solids with the remainder being the liquid portion of the slurry. More preferably, the slurry is about 40 to about 50 weight percent solids. This liquid used for the slurry is a liquid containing para-xylene. The amount of para-xylene in the liquid is an amount suitable for providing for the slurry of crystalline para-xylene and liquid at the temperature used for the slurry. Preferably, the liquid para-xylene used to prepare the slurry is about 70 to about 85 weight percent para-xylene. The remainder of the liquid is typically a mixture of ortho- and meta-xylene, ethylbenzene and minor amounts of other hydrocarbons present in the process. After the desired purity of crystalline para-xylene is achieved, the purified crystalline para-xylene is separated from the liquid and preferably washed with liquid para-xylene to remove adhering mother liquor. The liquid para-xylene used for the wash is preferably high purity para-xylene having a purity of at least about 99.7 weight percent, more preferably at least about 99.8 weight percent. The weight ratio of liquid para-xylene wash to crystalline para-xylene is typically about 0.05:1 to about 0.5:1, more preferably about 0.15:1 to about 0.25:1. Upon melting the purified crystalline para-xylene, a liquid product para-xylene having a purity of at least 99.7 weight percent, more preferably at least about 99.8 weight percent, and most preferably at least about 99.85 weight percent para-xylene is produced.

Figure 7:
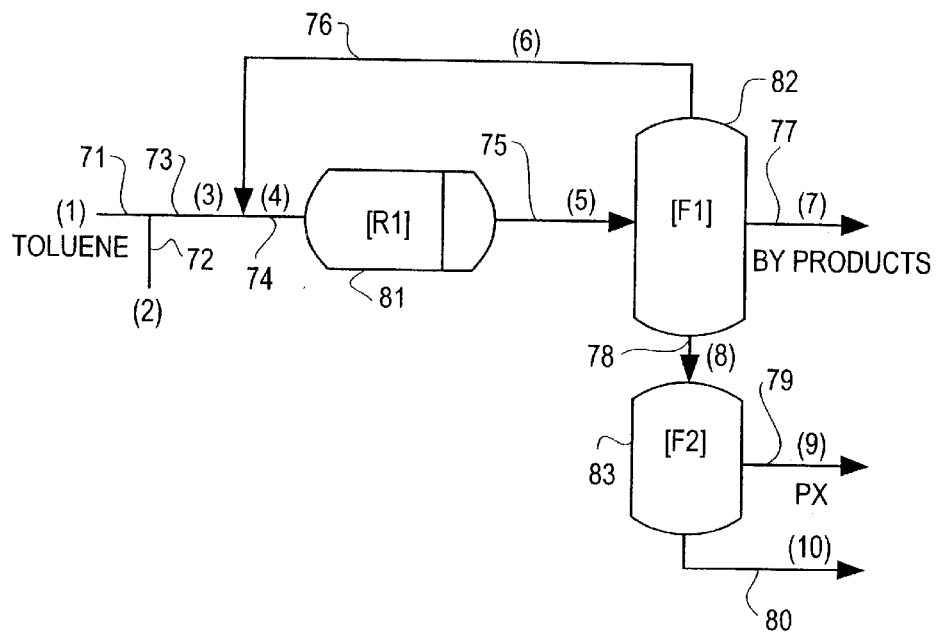
FIG. 7: shows a conventional or selective toluene conversion process for producing para-xylene (prior art).

FIG. 7 shows a schematic of a state of the art process for the production of PX from a toluene-containing feed in stream (1) in line 71 and, optionally, an additional feed in stream (2) in line 72 which typically may include hydrogen, C9 aromatics, mixtures of carbon oxides, or mixtures of hydrogen and the previous components. Stream (1) most preferably comprises pure toluene, but would typically comprise about 97 wt % to about 98 wt % toluene. The main impurities would be paraffins and naphthenes that boil in the same range, in addition to some benzene, xylenes, and ethylbenzene. Though not preferable, the composition of the toluene feed can be as low as 90 wt % toluene with the above-mentioned impurities. Non-limiting examples for the feeds in stream (2) include hydrogen methanol, C9 aromatics, mixtures of carbon oxides and hydrogen, or mixtures of hydrogen and the previous components. When the total feed (3) in line 73 is combined with a recycle stream comprising unreacted toluene feed (6) in line 76 which may also contain hydrogen and unreacted feed components from stream (2), it is then fed to a toluene conversion reactor R1 81 and contacted with a toluene conversion catalyst to covert the feed to a mixture of xylenes. Some ethylbenzene may also be formed; however, it is preferable to avoid production of ethylbenzene to the extent possible. Any of the toluene conversion processes disclosed above can be used in the toluene conversion process unit RI. The effluent (5) in line 75 which comprises xylenes and unreacted toluene feed is then sent to a separation process unit F1 82. Perhaps the most common example of a separation process for F1 is distillation, but both crystallization, SiMBAC or combinations of distillation with either crystallization or SiMBAC can also be employed in this role to achieve various benefits. The separation process conducted in F1 82 generates a recycle stream (6) in line 76 comprising unreacted toluene as well as hydrogen and any other unreacted feed components which is fed back to toluene conversion reactor R1 81; a by-product stream (7) in line 77, and a PX-containing stream (8) in line 78 which may also contain meta-xylene, ortho-xylene, ethylbenzene, with trace benzene, toluene and heavy aromatics. The by-products in stream (7), of course, depend on the nature of the process feed and type of catalyst, but one of the most common by-products is benzene. Para-xylene-containing stream (8) in line 78 is then sent to purification process unit F2 83 where the PX product (9) in line 79 is purified and any of the meta-xylene (MX), ortho-xylene (OX), ethylbenzene (EB), and other impurities, and possibly also a portion of the PX, are rejected in stream (10) in line 80. The purification process used in F2 83 may be crystallization or a SiMBAC-based process.

The process depicted in FIG. 7 adequately captures the state of the art for PX production from toluene. Both conventional and selective toluene processes are described by FIG. 7, and depending on the type of purification step used in F2, both crystallization and SiMBAC-based processes are described in the process design scheme illustrated in FIG. 7. For example if the purification process used in F2 is crystallization, FIG. 1 depicts a crystallization-based process that could be either conventional or pX-selective. If the purification process used in F2 is SiMBAC, FIG. 1 equally depicts a Parex-type process that is also either conventional or pX-selective. It is further understood that many toluene conversion-based, PX-producing facilities which use a process such as that illustrated in FIG. 7 are integrated with xylene isomerization or other petrochemical processes. Thus, portions of the respective processes can overlap within common equipment or various streams can be exchanged between the processes to improve overall yields and lower production costs for the integrated complex as a whole. The most common example involves the recycle and isomerization of the reject stream (10) in line 80 which comprises meta-xylene (MX), ortho-xylene (OX), ethylbenzene (EB), and other impurities, and possibly also a portion of the PX, to ultimately produce more PX.

Toluene Conversion with PSA Embodiment 1

Figure 8:
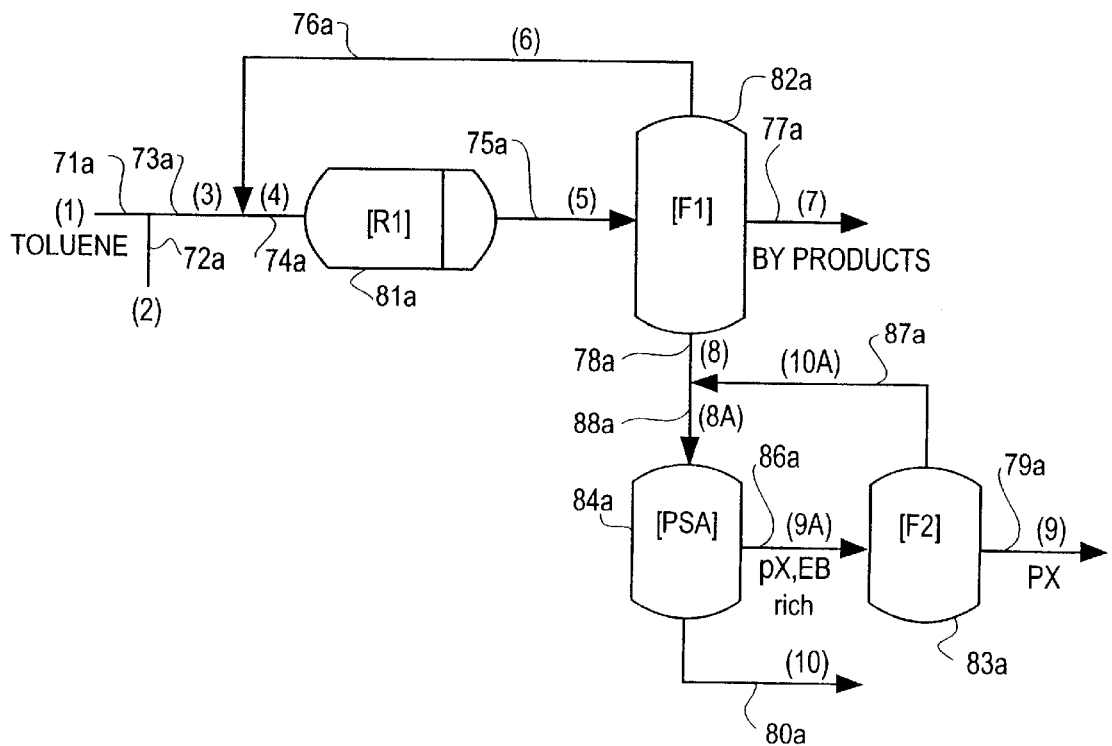
FIG. 8: shows an embodiment of the present invention in which a conventional or selective toluene conversion process for producing para-xylene incorporates pressure swing adsorption process separation technology.

An embodiment of the present invention is shown in FIG. 8. This process represents one embodiment where the PSA technology has been incorporated to perform a bulk separation of the PX-containing stream (8) in line 78a from the separation unit (F1) 82a prior to purification of the PX-rich product stream (9A) in line 86a. Provided the production of EB is negligible, the process in FIG. 8 would function for a selective or conventional toluene conversion process. The stream identification and process layout is generally similar to that described in FIG. 7; however, following the separation of the unreacted toluene, by-products, and other unconverted reactants from the mixed pX-containing stream produced by conversion of toluene, a PSA unit is incorporated to perform a bulk separation of pX/EB and produce a pX-rich effluent stream (9A) in line 79a having an enriched pX content. The PX-containing stream (8) in line 78a produced by conversion of a toluene-containing feedstream (1) followed by separation of the xylenes-containing effluent stream from the toluene conversion in separation process unit F1 82*a* is combined with a recycle stream (10A) from line 87*a* comprising MX, OX, and EB and is then sent to the PSA process unit 84*a* which produces a PX-rich stream (9A) in line 86*a*. The PX-rich effluent from the PSA process is then sent via line 86*a* to a purification process unit F2 83*a* for purification (generally by crystallization or simulated moving bed adsorption) while the impurities from the PSA process (which may include meta-xylene (MX), ortho-xylene (OX), ethylbenzene (EB), and other impurities, and possibly also a portion of the PX,)are rejected in stream (10) in line 80*a* and recycle stream (10A) in line 87*a*. Purified para-xylene product is collected in Stream (9) in line 79*a*.

Toluene Conversion-PSA Embodiment 2

Figure 9:
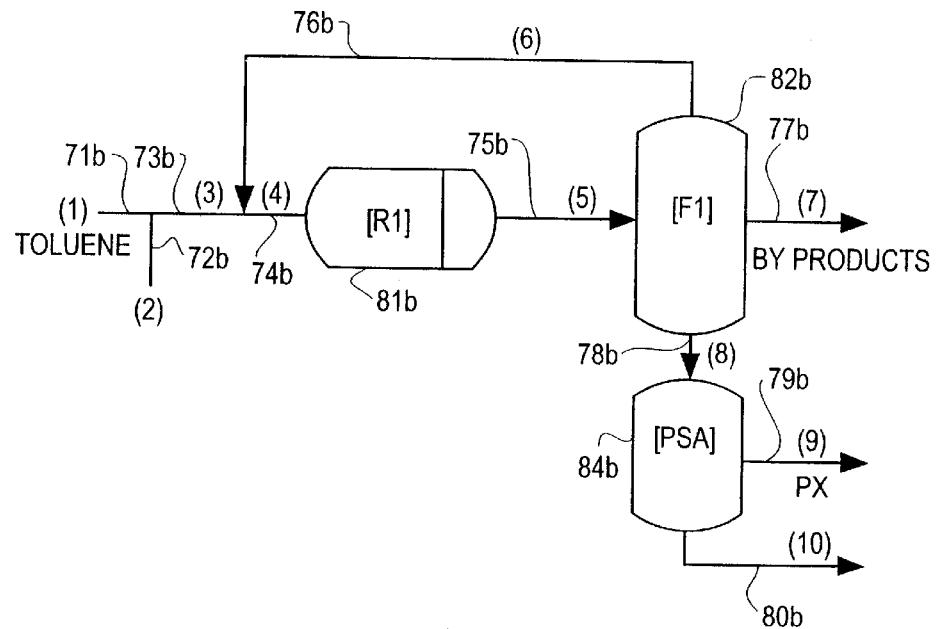
FIG. 9: shows an embodiment of the present invention in which a hybrid toluene conversion process for the production of para-xylene incorporates pressure swing adsorption process separation technology.

Another embodiment of the present invention is shown in FIG. 9. While this embodiment can also accommodate both conventional and selective toluene processes, it is particularly suited for use with selective toluene processes which produce an effluent primarily comprising PX. In the process embodiment of the present invention illustrated in FIG. 9, the main departure from the process shown in FIG. 8 is that the PX-containing stream (8) in line 78*b* from the separation unit F1 82*b* is fed directly to the PSA process unit 84*b* without combining it with a recycle stream. Subjecting the PX-containing effluent stream (8) to pressure swing adsorption produces product grade PX stream(9) in line 79*b* and a reject stream of impurities (stream 10) in line 80*b* comprising meta-xylene (MX), ortho-xylene (OX), ethylbenzene (EB), and other impurities, and possibly also a portion of the PX.

Toluene Conversion-PSA Embodiment 3

Figure 10:
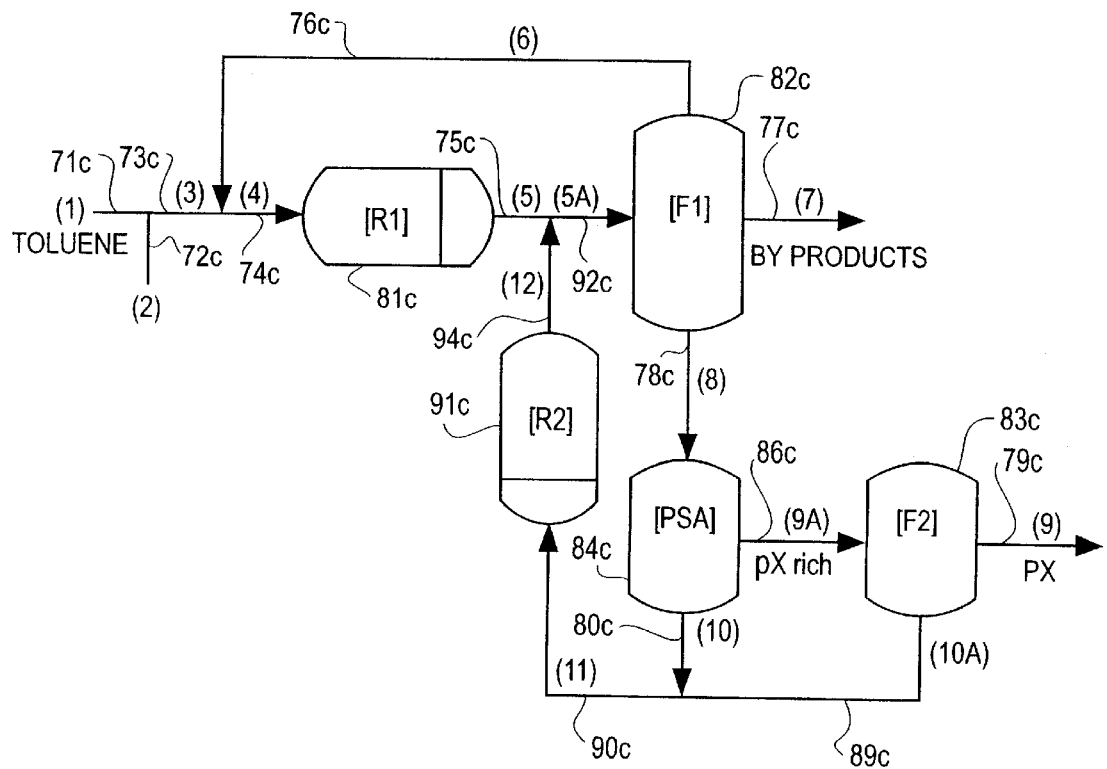
FIG. 10: shows an embodiment of the present invention in which a hybrid toluene conversion process for the production of para-xylene incorporates pressure swing adsorption process separation technology and is integrated with xylene isomerization.

FIG. 10 depicts another embodiment of the present invention where a xylene isomerization reactor is included. Such an embodiment, wherein the reject streams (10) and (10A) from the PSA process and purification step are isomerized to produce an effluent comprising an equilibrium mixture of xylenes which is combined with the effluent stream from the toluene conversion process and sent to the separation process F1, increases overall yield of PX. The reject stream (10) in line 80*c* will contain significant amounts of MX and OX. The reject stream (10A) in line 89*c* will also contain MX and OX, perhaps in addition to EB and some heavier aromatics. The combination of these streams (11) in line 90*c* is well suited for isomerization in a xylene isomerization reactor R2 91*c*; the effluent of which (stream 12) in line 94*c* is fed in combination with the toluene conversion reactor effluent (stream 5) in line 75*c* into separation process F1 82*c* via line 92*c*. Typical xylene isomerization reactor systems are described in patents U.S. Pat. Nos. 5,705,726; 4,899,011; WO 97/45385; and U.S. Pat. No. 6,051,744 all of which are incorporated herein by reference in their entireties. If the amount of EB fed and produced in the process is negligible, it would then be possible to combine the xylene isomerization reactor effluent (12) with stream (8) in line 78*c* from separation reactor F1 82*c* as feed to the PSA process. In such a case, an effective debottleneck could be accomplished without modification of the separation process F1.

Toluene Conversion-PSA Embodiment 4

Figure 11:
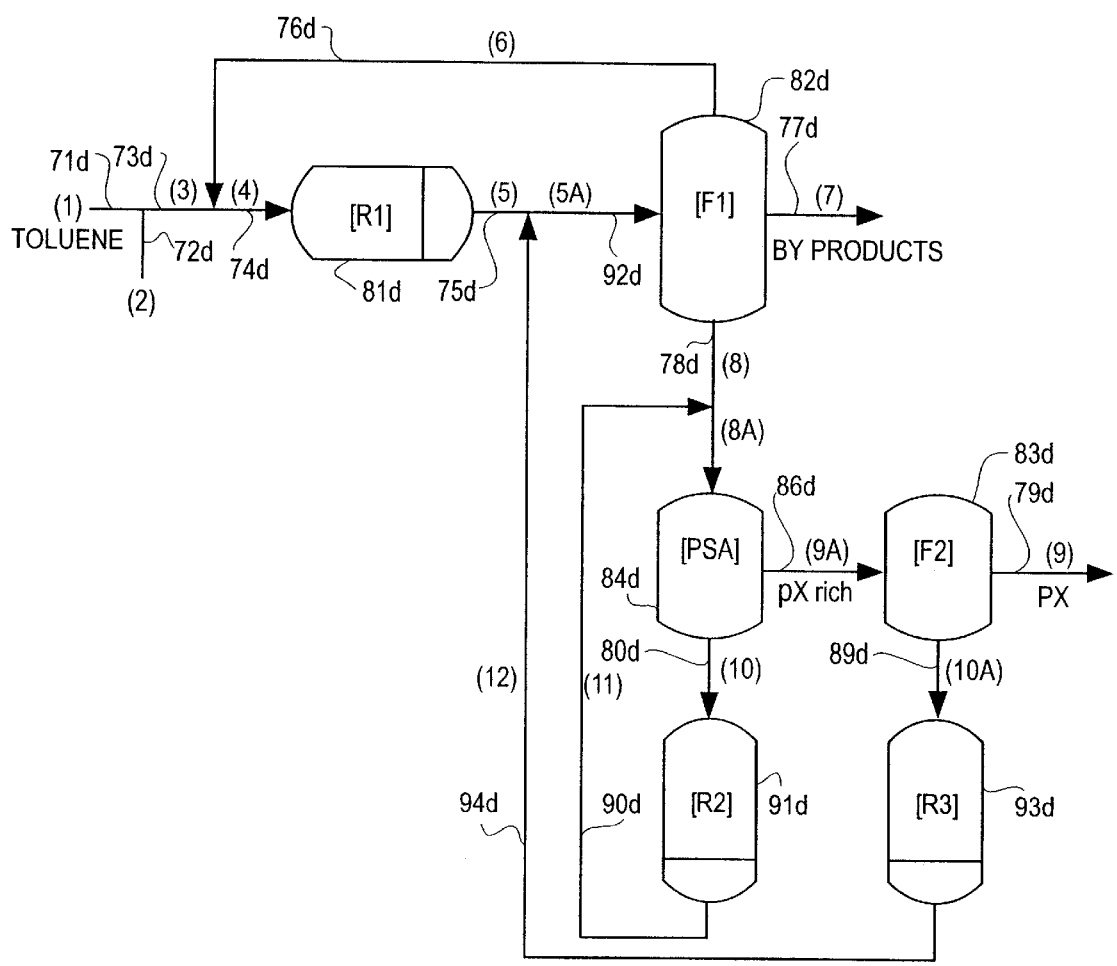
FIG. 11: shows an embodiment of the present invention in which a conventional toluene conversion process for the production of para-xylene incorporates pressure swing adsorption process separation technology and is integrated with xylene isomerization in multiple reactors.

The embodiment shown in FIG. 11 recognizes that the reject streams (10) in line 80*d* and (10A) in line 89*d* from the PSA process unit 84*d* and from the purification process unit F2 83*d* will have a different composition. The PSA reject stream (10) in line 80*d* will be predominantly composed of MX and OX while the reject stream from the F2 purification process (stream 10A) in line 89*d* may have EB as a significant component. Catalyst reactor R2 91*d* can then be optimized to perform xylene isomerization under relatively mild conditions and catalyst reactor R3 93*d* can be optimized to perform xylene isomerization under more severe conditions necessary to convert EB and other impurities. Thus, the R2 effluent stream (11) in line 90*d* can be recycled to the PSA unit 84*d* while the R3 effluent stream (12) in line 94*d* is recycled to separation process unit F1 82*d*. The advantage of this configuration over that presented in Embodiment 3 is that a smaller recycle stream (12) in line 94*d* is sent to separation process unit F1 82*d* and more specialized reactors can be employed to produce PX with a higher overall yield structure.

Catalysts suitable for use in isomerization reactor R2 and EB conversion reactor R3 are disclosed in U.S. Pat. Re No. 31,782, U.S. Pat. No. 4,899,011 and EP 0 923 512 all of which are incorporated herein by reference in their entireties. An example of a suitable isomerization catalyst is an aluminosilicate/borosilicate catalyst system with a molybdenum hydrogenation metal. Such catalysts are described in EP 0 923 512 incorporated herein by reference in its entirety.

The xylene isomerization catalyst is a catalyst that will catalyze the conversion of one xylene, such as meta-xylene or ortho-xylene, to another xylene, such as para-xylene. In particular, effective xylene isomerization catalysts will isomerize a mixture of xylenes where the xylenes are present in non-equilibrium amounts to a mixture containing, or very nearly containing, the xylenes in equilibrium amounts at the temperature used for the isomerization reaction. For example, a mixture of xylenes containing ortho-xylene, meta-xylene and para-xylene, where the para-xylene is present in less than the equilibrium amount, can be converted by an effective xylene isomerization catalyst to a mixture of xylenes where the ortho-, meta- and para-xylenes are present at or very near their equilibrium amounts.

The isomerization catalyst having activity for the isomerization of xylene is preferably, an acidic molecular sieve which is characterized by a constraint index in the approximate range of about 1 to about 12. Preferred molecular sieves are borosilicate molecular sieves or ZSM-type zeolite molecular sieves. The molecular sieve used is preferably dispersed on alumina, silica or another suitable matrix. The xylene isomerization catalyst may contain a hydrogenation metal selected from metals of groups VI and VIII of the Periodic Table of Elements.

The catalyst having activity for the conversion of ethylbenzene is preferably an acidic molecular sieve which is characterized by a constraint index in the approximate range of about 1 to about 12, more preferably it is a zeolite, preferably a crystalline aluminosilicate zeolite having a particle size of at least about 1 micron. The EB conversion catalyst may contain a hydrogenation metal selected from metals of groups VI and VIII of the Periodic Table of Elements.

The ethylbenzene conversion catalyst is a catalyst that selectively catalyzes the conversion of ethylbenzene in the feed mixture to another compound or compounds that can easily be removed from the product mixture. For example, within the scope of the invention, ethylbenzene conversion can occur by, but is not limited to, a transalkylation or disproportionation reaction whereby the ethylbenzene is catalytically converted to benzene and diethylbenzene, or an ethyl group from ethylbenzene is transferred to a xylene molecule thereby forming conversion products that are easily removed from the product mixture. Ethylbenzene conversion can also occur by a deethylation reaction, whereby the ethylbenzene is catalytically converted to benzene and a mixture of ethylene and ethane.

Ethylbenzene conversion catalysts suitable for use in the present invention include but are not limited to Al-MFI molecular sieve dispersed on silica and large particle size molecular sieves, particularly a ZSM-5-type of molecular sieve having a particle size of at least about 1 micron, dispersed on silica, alumina, silica/alumina or other suitable support. The support material is preferably silica. Suitable catalysts based on a ZSM-type molecular sieve, for example, ZSM-5 molecular sieves, are described in U.S. Pat. Re. No. 31,782, which is incorporated herein by reference in its entirety. Other methods known to those skilled in the art, for example reaction of or coating with silicones, resulting in an XIA_parameter to EBA_parameter ratio of no more than 10, are also within the scope of the invention.

The isomerization catalyst and EB conversion catalysts used in the above embodiments of the present invention preferably contain a hydrogenation metal, such as molybdenum, platinum, palladium, rhodium, ruthenium, nickel, iron, osmium, iridium, tungsten, rhenium, and the like, dispersed on a suitable matrix. Suitable matrix materials include, but are not limited to, alumina and silica.

The above embodiments demonstrate the advantages of combining pressure-swing adsorption with toluene conversion for production of para-xylene. The advantages of this new process include lower capital and energy costs, and higher yields of xylene.

The following examples will serve to illustrate certain embodiments of the invention disclosed herein. These examples should not, however, be construed as limiting the scope of the novel invention as there are many variations which may be made thereon without departing from the spirit of the disclosed invention, as those of skill in the art will recognize.

Experimental Equipment

A mass flow controller determines the Helium flow rate. A saturated flow of He, which contains EB and xylenes, is passed over the bed of adsorbent heated to the adsorption temperature. At the outlet of the bed, the gas stream is analyzed by gas chromatography to determine the composition. Any compounds not adsorbed are collected in a trap filled with silica gel with pores large enough to adsorb all compounds. After the adsorbent bed is saturated, the saturator is by-passed delivering only He to the adsorbent bed. The sample receiver is switched to a second silica gel adsorbent bed and the temperature is increased to 250° C. to affect desorption. After desorption, the receivers are removed and weighed. The receivers are then heated to desorb the adsorbed hydrocarbons, which are collected in a cold trap and subsequently analyzed by gas chromatography.

Adsorbents (1) HZSM-5

H-ZSM-5 containing 2% Al was a commercial sample (CBV-3020) obtained from PQ Corporation (Valley Forge Executive Mall, PO Box 840, Valley Forge, Pa. 19482).). An SEM micrograph of the sieve powder is shown in FIG. 12.

(2) HZSM-5

A second sample of HZSM-5 was prepared according to the following procedure: 20.66 g of NaOH was dissolved in 560.3 g distilled water, followed by 10.6 g of sodium aluminate ($Na_2O \cdot Al_2O_3 \cdot 3H_2O$) and 98.13 g tetrapropylammonium bromide (TPABr). The mixture was stirred until a clear solution formed. 485.9 g Nalco 2327 silica sol (40 wt % $SiO_2$) was then added and the mixture stirred for two hours. The pH of the resulting mixture was 12.5. The mixture was transferred to a Teflon-lined Parr reactor and heated at 300° F. (150° C.) for seven days with stirring (275 rpm). The reaction mixture was cooled and filtered, and the solid product washed with 10 L of distilled water. The zeolite powder was calcined to remove the template using the following program: Dry at 329° F. (165° C.) for 4 hr.; ramp to 950° F. (510° C.) over 4 hr.; hold at 950° F. (510° C.) for 12 hr.; ramp back to ambient temperature over 4 hr. An SEM micrograph of the sieve powder is shown in FIG. 7.

(3) Na-ZSM-5

Sample (2) was $Na^+$ exchanged by heating 50 g of the sieve in a solution of $NaNO_3$ (50 g in 500 ml distilled water) at 175° F. (80° C.) with stirring. The sieve was filtered and the exchange repeated with the addition of adjusting the pH to 9.5 with 50% NaOH solution. Again, the sieve was filtered and then washed by stirring for one hour in distilled water (500 ml) heated at 175° F. (80° C.). The sample was calcined using the same temperature program described above, except holding at 950° F. (510° C.) for four hours. Elemental analysis of this sample gave 1.84 wt % Na and 1.3 wt % Al. The washing step was repeated three more times to remove the excess $Na^+$. The final sample was dried for 5 hours at 220° F. (105° C.). Elemental analysis by ICP showed the washed zeolite to have 1.3 wt % Al and 1.2 wt % Na, which is a 5% molar excess of Na.

(4) Silicalite

Silicalite was prepared by adding 18.4 g NaOH to 227.6 g $H_2O$. After dissolution, 12.8 g tetrapropylammonium bromide was dissolved and 122.6 g Nalco 2327 silica sol was added and stirred for 2 hours. Concentrated $H_2SO_4$ was slowly added to achieve a pH of 13. The resulting solution was heated under autogenous pressure in a Teflon-lined autoclave for 1–7 days at 300° F.(150° C.). The crystals were filtered and washed to a neutral pH filtrate. An SEM micrograph of the sieve powder is shown in FIG. 8.

(5) Silicalite

A second sample of silicalite comprising crystals ~0.1 micron in size was prepared according to the following procedure: 1.72 g of NaOH was dissolved in 120 ml of a 1.0 M solution of tetrapropylammonium hydroxide (TPAOH). 30.0 g Cab-o-Sil M-5 silica was then added to the solution, forming a slurry. The slurry was stirred at 175° F. (80° C.) until a clear solution formed. Additional distilled water was added to make up any losses due to evaporation. The solution was transferred to a Teflon-lined Parr reactor and heated at 300° F. (150° C.) for 24 hours. The resulting mixture was centrifuged and the solids layer redispersed in distilled water. This process was repeated until the pH of the silicalite sol was <9. A portion of the silicalite sol was dried and calcined using the procedure described for sample (2), in order to obtain a solid sample for the adsorption experiments. A TEM micrograph of the sieve crystals dispersed in water is shown in FIG. 9.

(6) Ti-MFI (TS-1)

182.4 g of tetraethylorthosilicate and 2.53 g of tetraethylorthotitanate were mixed with 400.23 g of tetrapropylammonium hydroxide (20% in water). In order to remove the ethanol, the mixture was heated at 175–195° F. (80–90° C.) for 5 hours with stirring. After cooling the mixture to ambient temperature, the volume of the mixture was diluted to 600 ml with distilled water. The mixture (pH=12) was heated at 350° F. (175° C.) for 14 days with stirring (~270 rpm). The white powder was washed with distilled water and calcined using the procedure described for sample (2). An SEM micrograph of the sieve powder is shown in FIG. 10.

(7) ZSM-22

4.7 g of NaOH was dissolved in 119 g of distilled water. 640 g of MeOH and 220 g of Nalco 2327 silica sol (nominally 40 wt % $SiO_2$) were then added. The mixture was transferred to a 2 L autoclave and heated at 320° F. (160° C.) for 28 hours with stirring (~150 rpm). The product was collected by filtration and washed with 16 L of distilled water and calcined using the procedure described for sample (2). An SEM micrograph of the sieve powder is shown in FIG. 11.

EXAMPLE 1

Determination of $C_8$ Aromatic Adsorption Capacity of Silicalite

Figure 6:
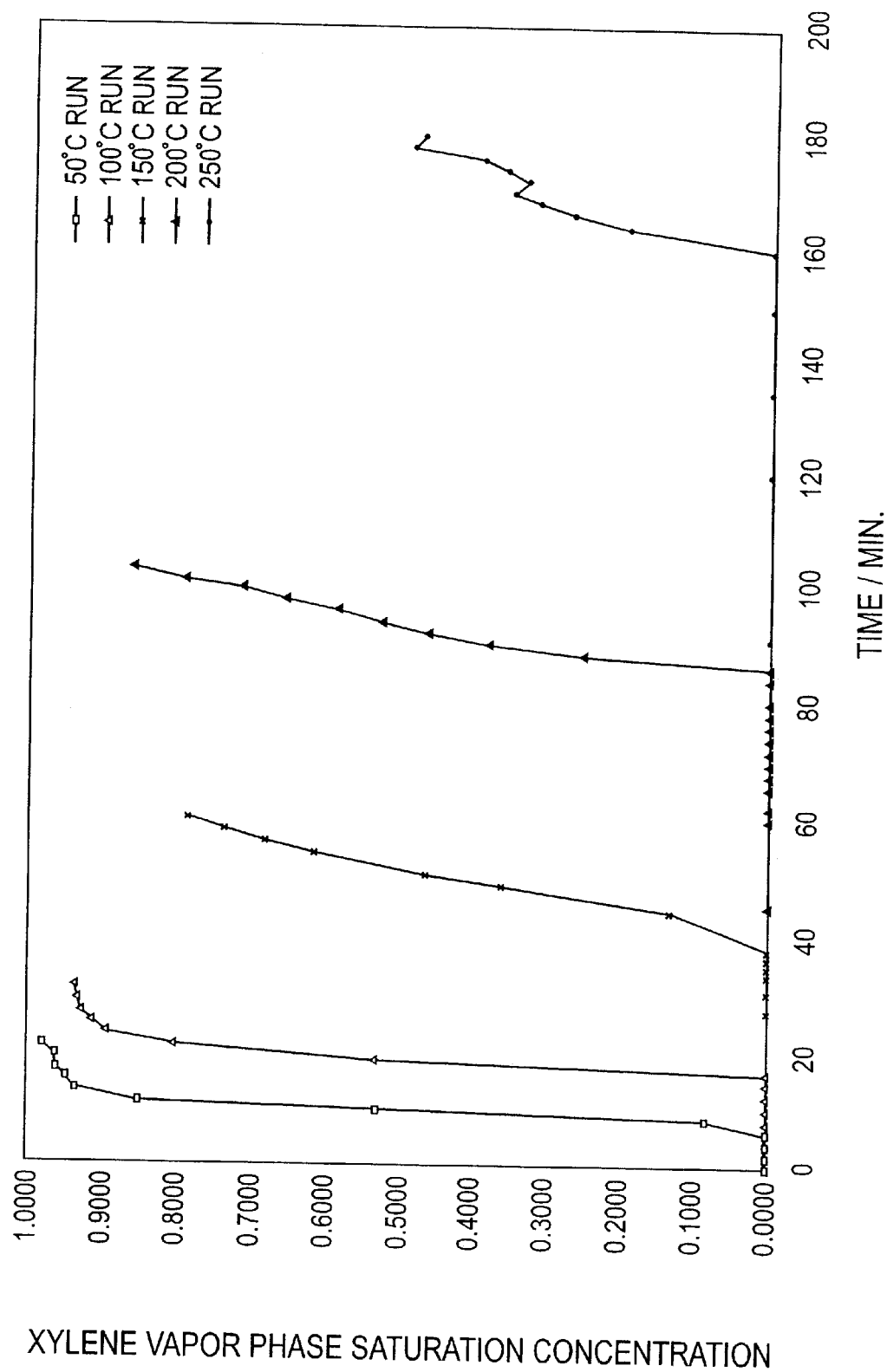
FIG. 6 shows a graph of Xylene Vapor Phase Concentrations vs. Adsorbance Time.

When a saturated stream of pX (or EB) is passed over H-ZSM-5 or silicalite at low temperature there is nearly complete adsorption. At the inlet to the reactor the concentration is equivalent to the vapor pressure, while at the outlet of the bed little pX can be detected. At saturation, the bed can no longer adsorb pX, and the concentration at the bed outlet quickly increases to the inlet concentration, as shown in FIG. 6. The amount adsorbed is proportional to the product of the flow rate, concentration and time, equation 1.

$$g\ adsorbed = [He\ flow\ (cc/min) \times Conc(torr/760\ torr/atm) \times 1\ atm \times t(min) \times 106\ g/mol]/22400\ cc/mol \quad (1)$$

With increasing temperature the amount of pX adsorbed on silicalite decreases as shown in Table 1. At 50° C. and a pX partial pressure of 6 torr (0.8 kPa), the saturation adsorption capacity was measured to be 9.2 wt % (92 mg/g) pX on silicalite (Adsorbent 4), while at 250° C. the adsorption capacity decreases to 0.3 wt % (3 mg/g).

TABLE 1

Adsorption of para-Xylene by Silicalite at Atmospheric Pressure (6 torr pX; 0.8 pKa)

| Adsorption Temperature, ° C. | Adsorption Capacity (mg pX/g silicalite) |
|---|---|
| 50 | 92 |
| 100 | 49 |
| 150 | 24 |
| 200 | 10 |
| 250 | 3 |

Single component adsorption capacities were also measured for mX, oX and EB. A comparison of the single component saturation adsorption capacity of pX, EB, mX and oX measured at 50° C. is shown in Table 2. The data demonstrates that silicalite (Adsorbent 4) has a much higher adsorption capacity for pX and EB than it does for mX and oX.

TABLE 2

Adsorption Capacity at 50° C. and atmospheric pressure (6 torr; 0.8 pKa)

| $C_8$ Aromatic Isomer | Adsorption Capacity (mg/g silicalite) |
|---|---|
| pX | 92 |
| EB | 63 |
| oX | <2 |
| mX | <2 |

EXAMPLE 2

Separation of para-Xylene from ortho-Xylene with Silicalite (Adsorbent 4)

A 1:1 mixture (3 torr:3 torr) of para-xylene and ortho-xylene was passed over the silicalite (4) adsorbent at 50° C. Monitoring the outlet stream by gas chromatography (GC) indicated that pX was adsorbed by the silicalite. Essentially ortho-xylene was not adsorbed by the silicalite, but rather passed through and was collected in a downstream trap containing amorphous silica adsorbent. Before the silicalite bed was completely saturated with para-xylene (i.e., pX breakthrough was not yet observed), the flow of xylenes was discontinued and He purged through the bed. The effluent stream was then directed to a second amorphous silica-containing trap, and the temperature of the silicalite bed was increased to 300° C. to desorb the xylenes. The adsorbed materials were recovered from the two amorphous silica traps and analyzed for xylenes by GC. The analyses are given in Table 3. The results show that para-xylene is selectively adsorbed on silicalite while ortho-xylene is essentially not adsorbed. The amount of para-xylene adsorbed was 89 mg/g which is slightly below the adsorption capacity.

TABLE 3

Silicalite: Separation of pX/oX (3 torr/3torr)at 50° C. and Atmospheric Pressure

| Not Adsorbed | Adsorbed | Adsorbed, mg/g |
|---|---|---|
| 99% oX (0.3% pX) | 97.6% pX (2.1% oX) | 89.0* (8.9 wt %) |

*Adsorption not run to saturation.

EXAMPLE 3

Separation of $C_8$ Aromatic Mixtures with Silicalite (Adsorbent 4)

A 1:1:1:1 mixture of pX:EB:mX:oX (8 torr total $C_8$) produced by bubbling He through an equimolar mixture of pX, EB, mX, and oX at atmospheric pressure)was passed over the silicalite (4) adsorbent at 50° C. Essentially mX and oX were not adsorbed on the silicalite, but passed through and were collected into the first silica trap. When the silicalite bed became saturated with pX and EB, the flow of xylenes was discontinued and He purged through the bed. The effluent was then switched to the second silica trap and the temperature of the silicalite bed increased to 300° C. to desorb the adsorbed hydrocarbons. The adsorbed materials were recovered from the two silica beds and analyzed for $C_8$ aromatics. The analysis is given in Table 4. The results show that in a mixture of EB and xylenes, pX and EB are selectively adsorbed on silicalite, while mX and oX are essentially not adsorbed.

TABLE 4

Silicalite: Separation of $C_8$ Aromatics at 50° C. and atmospheric pressure (8 torr)

| Not Adsorbed Composition | Adsorbed Composition | Wt % Adsorbed |
|---|---|---|
| 2.6% pX | 45.7% pX | 6.5% (pX and EB) |
| 5.5% EB | 51.4% EB | |
| 52.4% mX | 1.4% mX | |
| 39.2% oX | 1.1% oX | |

EXAMPLE 4

Comparison with HZSM-5: Adsorption of EB and Xylenes on H-ZSM-5 (Adsorbent 1) (CBV-3020), Following the procedure described in Example 1, the saturation adsorption capacity of H-ZSM-5 (Adsorbent 1)

was determined. Table 5 compares the saturation adsorption capacity of pX, EB, mX and oX at 50° C. The table demonstrates that for H-ZSM-5, pX and EB have a much higher adsorption capacity than mX and oX, although there is significant adsorption of the latter two.

TABLE 5

H-ZSM-5 (1): Adsorption Capacity at 50° C. and atmospheric pressure (8 torr)

| $C_8$ Aromatic Isomer | Adsorption Capacity | |
|---|---|---|
|  | (Wt %) | (mg/g) |
| pX | 9.0 | 90 |
| EB | 7.5 | 75 |
| oX | 4.0 | 40 |
| mX | 4.0 | 40 |

EXAMPLE 5

Separation of Mixtures with H-ZSM-5 (Adsorbent 1). Prior Art

A 1:1:1:1 mixture (8 torr total) of pX:EB:mX:oX was passed over the H-ZSM-5 (Adsorbent 1) adsorbent at 50° C. After saturation, the flow of xylenes was discontinued and He purged through the bed. The effluent was switched to the second bed of silica and the temperature in the H-ZSM-5 bed was increased to 300° C. to desorb the xylenes adsorbed. The products were recovered and analyzed for xylenes. The analysis of the $C_8$ aromatics adsorbed on H-ZSM-5 are given in Table 6 along with results for silicalite (Adsorbent 4), under the same conditions. The results show that for the material desorbed from H-ZSM-5, the pX and EB concentrations are much lower, mX and oX are higher, and small amounts of benzene (Bz), toluene (Tol) and $C_9$ aromatics are present, indicating that some adsorbed xylenes reacted on the acid sites during high temperature desorption.

TABLE 6

Separation of $C_8$ Aromatics at 50° C. and atmospheric pressure (6 torr)

| Composition of Material Desorbed from Silicalite (4) Example 3 | Composition of Material Desorbed from H-ZSM-5 (1) Example 5 |
|---|---|
| — | 5.5% Bz |
| — | 5.9% Tol |
| 45.7% pX | 20.1% pX |
| 51.4% EB | 33.6% EB |
| 1.4% mX | 22.9% mX |
| 1.1% oX | 10.7% oX |
| — | 0.9% $C_9$ |

EXAMPLE 6

Comparison: Reaction of Adsorbed $C_8$ Aromatics on H-ZSM-5 (Adsorbent 1),

Desorption products from H-ZSM-5 (Example 5) suggest that aromatics react with acid sites in H-ZSM-5 at high desorption temperatures. To confirm, para-xylene was adsorbed at 50° C., atmospheric pressure and 6 torr partial pressure on silicalite (Adsorbent 4) and H-ZSM-5 (Adsorbent 1). The adsorbed pX was recovered by heating to 300° C. Analysis of the reaction products is given in Table 7 and indicates that there is substantial isomerization (pX to mX and oX) and transmethylation [pX to toluene and $C_9$, such as trimethylbenzene (TMB)] over H-ZSM-5, whereas, no reaction occurred over silicalite.

TABLE 7

Reactivity of Adsorbed pX

| Composition of Material Desorbed from Silicalite (4) | Composition of Material Desorbed from H-ZSM-5 (1) |
|---|---|
| pX 100% | Bz 0.1% |
|  | Tol 2.1% |
|  | pX 78.1% |
|  | mX 14.3% |
|  | oX 4.0% |
|  | TMB 1.2% |

EXAMPLE 7

Adsorption/Desorption of Olefins on Silicalite and H-ZSM-5

The effect of trace olefins, which are always present in the reactants in commercial feedstreams, on the adsorption capacity was evaluated by saturation of H-ZSM-5 (Adsorbent 1) and silicalite (Adsorbent 4) at room temperature with propylene, Table 8. The quantity of adsorbed hydrocarbon was determined at temperatures up to 200° C. H-ZSM-5 readily adsorbs about 7 wt % propylene at room temperature. As the temperature increases, some propylene desorbs. Even at 200° C., however, 10% of the initial amount adsorbed remains. In order to keep olefins from lowering the adsorption capacity of H-ZSM-5 it will be necessary to operate at temperatures of above about 450° F. (about 230° C.). At these temperatures, however, significant reactions occur leading to poor selectivity. At lower temperature, desorption times are very long and olefins will reduce the adsorption capacity. In contrast silicalite does not adsorb olefins even at room temperature, thus the adsorption capacity will be unchanged with repeated adsorption/desorption cycles. The adsorption capacity of silicalite is unchanged after more than 25 adsorption/desorption cycles.

TABLE 8

Adsorption of Propylene

| Temp. | H-ZSM-5 (1) | Silicalite (4) |
|---|---|---|
| 20° C. | 6.9 wt % | 0 wt % |
| 100° C. | 5.2 wt % | — |
| 150° C. | 2.7 wt % | — |
| 200° C. | 0.6 wt % | — |

EXAMPLE 8

Effect of Xylene Partial Pressure on Adsorption Capacity at Elevated Pressure

In order to rapidly desorb para-xylene and ethylbenzene, the desorption temperature should be above about 450° F. (about 230° C.). At low partial pressure, however, the adsorption capacity is low, as seen in Table 1. The adsorption capacity at elevated temperature can be increased by increasing the adsorbate (pX and EB) partial pressure. In order to increase the pX partial pressure, the xylene saturator was replaced by an ISCO syringe pump. Additionally, a 6-way valve, heat tracing and other minor modifications were required to give instant vaporization of the xylene.

Table 9 gives the adsorption capacity of pX on silicalite (Adsorbent 4) at different temperatures and partial pressures. The data show that at constant partial pressure, the amount of pX adsorbed decreases with increasing temperature. Whereas, at high temperature, the amount of pX adsorbed can be increased by increasing the partial pressure of pX.

TABLE 9

Adsorption of pX by Silicalite at Various Temperatures and Pressures

| Ppx, torr | Temperature, °C. | mg pX adsorbed per gram silicalite |
|---|---|---|
| 6 | 50 | 92 |
| 6 | 100 | 49 |
| 6 | 150 | 24 |
| 6 | 200 | 10 |
| 6 | 250 | 4 |
| 500 | 250 | 20 |
| 888 | 250 | 29 |
| 1996 | 250 | 60 |

EXAMPLE 9

Separation of $C_8$ Aromatic Mixtures with Silicalite at Elevated Pressure

A 1:1:1:1 mixture of pX:EB:mX:oX at a total pressure of 89 psig and 38.6 psi partial pressure of $C_8$ aromatics (1995 torr) was passed over the silicalite (4) adsorbent at 250° C. The effluent composition was monitored by gas chromatography (GC). As in Example 1, when the silicalite adsorbent bed is saturated with a given isomer, the concentration of that isomer in the vapor phase at the bed outlet quickly increased to the inlet vapor phase concentration. The time required to detect that isomer at the bed outlet is proportional to the amount adsorbed on the bed.

The amount of mX and oX adsorbed was relatively small, while significantly larger amounts of pX and EB were adsorbed, Table 10. The results show that pX and EB can be selectively adsorbed at elevated temperatures and pressures in an amount comparable to pX alone (Example 8) at the same partial pressure.

TABLE 10

Adsorption Capacity of $C_8$ Aromatics at 250° C. and 1996 torr Partial Pressure (pX partial pressure about 500 torr)

| mX | 3 mg/g |
|---|---|
| oX | 3 mg/g |
| pX | 21 mg/g |
| EB | 22 mg/g |

EXAMPLE 10

Comparison of Silicalite and NaZSM-5

Non-Acidic NaZSM-5

Since HZSM-5 isomerizes and transmethylates the adsorbed xylenes, a non-acidic, sodium exchanged sample was prepared and tested. It was found that CBV-3020 could not be completely exchanged; therefore, another sample of HZSM-5 (Adsorbent 2), was prepared containing 1.3 wt % Al. This material was completely exchanged with Na, such that no acid sites remained to give Na-ZSM-5(Adsorbent 3). The adsorption capacity for pX was 115 mg/g at 50° C. and atmospheric pressure. Increasing the temperature to 250° C. decreased the adsorption capacity to 26.3 mg/g. Furthermore, at 250° C., only pX was observed in the effluent, confirming complete exchange of the acid sites with $Na^+$.

This sample was also tested with a saturated gas mixture (1 atm) of C8 aromatics in He at 50° C., as was done with silicalite and HZSM-5. The adsorbate was desorbed and analyzed by GC. A comparison of these results with those obtained for silicalite (Adsorbent 4) is given in Table 11. The mX and oX present in the desorbate for NaZSM-5 is not due to isomerization (as verified with the feed containing only pX). Thus, the NaZSM-5 sample has a lower pX adsorption selectivity than the silicalite sample tested, but a greater total capacity at these conditions.

To determine whether the decrease in pX selectivity is due to decreasing crystal size, a silicalite sample (Adsorbent 5), having a crystal size of approximately 0.1 μm was also prepared and tested. The composition of the adsorbate is compared with that of the adsorbates obtained for large crystal silicalite (Adsorbent 4), small crystal HZSM-5 (Adsorbent 1), and small crystal NaZSM-5 (Adsorbent 3) in Table 12. The size of the small crystal silicalite sample was determined by Transmission Electron Microscopy (TEM) to be approximately 0.1 μm. The crystal size of the two ZSM-5 samples was determined by Scanning Electron Microscopy (SEM) to be approximately 0.1–0.4 μm. The size of the large crystal silicalite sample was also determined by SEM to have an average minimum dimension of greater than 0.5 μm.

TABLE 11

Comparison of Silicalite and NaZSM-5
(Feed is a He stream saturated with $C_8$ aromatics (oX, mX, pX, and EB); adsorbed at 50° C. and 1 atm)

| Silicalite (4) | NaZSM-5 (3) |
|---|---|
| 65 mg adsorbate/g Silicalite | 88 mg adsorbate/g NaZSM-5 |

| Adsorbate Compositions | |
|---|---|
| 1.4% mX | 9.5% mX |
| 1.1% oX | 7.7% oX |
| 45.7% pX | 45.0% pX |
| 51.4% EB | 37.8% EB |

TABLE 12

Comparison of Adsorbates for Large Crystal Silicalite with Small Crystal Silicalite, HZSM-5, and NaZSM-5 at 50° C. and 1 atm.
(Feed is a He stream saturated with $C_8$ aromatics (oX, mX, pX, and EB);

| Silicalite (4) (>0.5 μm average minimum dimension) 65 mg adsorbate/ g Silicalite | Silicalite (5) (about 0.1 μm) 83 mg adsorbate/ g Silicalite | HZSM-5 (1) (about 0.1–0.4 μm) 85 mg adsorbate/ g HZSM-5 | NaZSM-5 (3) (about 0.1–0.4 μm) 88 mg adsorbate/ g NaZSM-5 |
|---|---|---|---|
| Adsorbate Compositions | | | |
| 1.4% mX | 14.8% mX | 17.0% mX | 9.5% mX |
| 1.1% oX | 13.7% oX | 14.3% oX | 7.7% oX |
| 45.7% pX | 33.3% pX | 31.4% pX | 45.0% pX |
| 51.4% EB | 38.2% EB | 37.3% EB | 37.8% EB |

The selectivities for the small silicalite, HZSM-5 and NaZSM-5 are very similar, with the selectivity of the NaZSM-5 sample for pX being somewhat better. All of these selectivities are significantly lower than that obtained for the large crystal silicalite. These results are consistent with a crystal size effect on selectivity.

EXAMPLE 11

Selective Adsorption with TS-1 (Ti-MFI) and ZSM-22

Using the same method as given in Example 3, the adsorption capacity at 50° C. and 8 torr total $C_8$ aromatics was measured for TS-1 (Adsorbent 6) and ZSM-22 (Adsorbent 7). Both samples showed selective adsorption of pX and EB over mX and oX. Results are given in Table 13.

TABLE 13

Adsorption on TS-1 and ZSM-22
Feed is a He stream saturated with $C_8$ aromatics (oX, mX, pX, and EB); adsorbed at 50° C. and 8 torr $C_8$ aromatics

| TS-1 (6) 58 mg adsorbate/g sieve | ZSM-22 (7) 46 mg adsorbate/g sieve |
|---|---|
| Adsorbate Compositions | |
| 3.1% mX | 4.8% mX |
| 3.3% oX | 5.4% oX |
| 42.8% pX | 39.9% pX |
| 50.8% EB | 50.0% EB |

EXAMPLE 12

This example illustrates that the pX-depleted stream gives lower xylene loss in the isomerization reactor, which increases the overall yield of pX for the unit."

A comparison was done for a xylene isomerization catalyst run with a mixed xylene feed containing 10 wt % pX and a mixed xylene feed containing 1 wt % pX. The catalyst was an aluminosilicate/borosilicate catalyst system with a molybdenum hydrogenation metal. Such catalysts are described in EP 0 923 512 incorporated herein by reference in its entirety. Results in Table 14 below show that xylene loss decrease when the amount of pX in the feed is reduced.

TABLE 14

|  | Feed A | Feed B |
|---|---|---|
| wt % pX in feed | 1% | 10% |
| % Xylene Loss at 50% EB conversion | 0.7 | 1.1 |
| % Xylene Loss at 80% EB conversion | 1.8 | 2.3 |

EXAMPLE 13

The data in Table 15 below show an example of a selective toluene catalyst based on an acidic MFI molecular sieve. The toluene feed had a purity of greater than 99.3%.

TABLE 15

|  | Temp [° F.] | Pres [psig] | H2/HC [mol/mol] | WHSV [hr$^{-1}$] | PX/X [%] | Net TMB | Net EB |
|---|---|---|---|---|---|---|---|
| Catalyst I | 720 | 227 | 4.0 | 1.8 | 40. | 0.01 | <0. |

Catalyst I would be appropriate for reactor R1 in Embodiments 1, 2 and 3 of the toluene conversion-PSA process of the present invention. Particularly important for Embodiment 2 of the toluene conversion-PSA process of the present invention is the net consumption of EB. In this manner, the PSA technology may be used exclusively for the production of PX without the necessity of additional purification.

EXAMPLE 14

Using a commercial xylene isomerization catalyst [a 20% borosilicate molecular sieve with 80% γ-alumina binder and molybdenum as the hydrogenation metal] as described in EP 0923 512, incorporated herein by reference, at 600° F. at 150 psig with a H2/HC of 4 and a WHSV of 2–30, the data in Table 16 below were obtained.

To avoid the build-up of EB in recycle streams of most PX production processes, EB must be separated or converted. The extent of EB conversion is often used as a measure of reaction severity. Higher severity implies either higher temperature or lower WHSV. The extent of xylene isomerization reaction is typically described as a Percent Approach to Equilibrium, or PATE, according to the following formula:

$$PATE = 100 \times \frac{(PXout - PXin)}{(PXeq - PXin)}$$

where PXin is the feed weight fraction of PX among the xylene isomers PX, MX, and OX. PXout is the corresponding quantity for the reactor effluent. PXeq is the equilibrium weight fraction of PX among the xylene isomers at reaction conditions. A PATE value of 100% implies that isomerization has proceeded to the maximum amount of PX that can be produced by thermodynamic equilibrium whereas lower values imply that further exposure to catalyst would produce more PX. Finally, the Net trimethylbenzene (TMB) is an indicator of the extent of xylene disproportionation reaction, a significant source of yield losses in most PX production processes.

TABLE 16

| Case | EB Conversion [%] | PATE [%] | Net TMB |
|---|---|---|---|
| I | <2 | 80 | <0.02 |
| II | 2 | 90 | 0.03 |
| III | 14 | ~100 | 0.25 |

It can be seen in Cases I and II that at fairly mild conditions, as indicated by the low EB conversion, that the PATE is significant while the production of TMB is minor. However, at the more severe conditions of Case III, losses to TMB become much more significant while the PATE reaches its maximum value.

With such low yield losses to TMB, Cases I and II represent an atypical operation of a xylene isomerization reactor that would be well suited for use in reactor R2 of Embodiment 4 of the toluene conversion-PSA process of the present invention. Because of the need to convert EB, Case III represents more conventional operation of a xylene isomerization reactor and would be more appropriate for use in reactor R3 of Embodiment 4.

That which is claimed is:

1. A process for the production of para-xylene from a feed comprising toluene comprising:
   (1) subjecting the toluene feed to toluene conversion to produce a xylene-containing effluent stream comprising para-xylene, meta-xylene, ortho-xylene, ethylbenzene, unreacted toluene, and other unconverted reactants,
   (2) separating unreacted toluene and the other unconverted reactants from the xylene-containing effluent stream from step (1) to produce a para-xylene-containing stream comprising para-xylene, meta-xylene, ortho-xylene, and ethylbenzene and converting the para-xylene-containing stream to a gaseous mixture comprising para-xylene, meta-xylene, ortho-xylene, and ethylbenzene; and (3) subjecting the gaseous mixture to a pressure swing adsorption process for separating para-xylene from a feed comprising the gaseous mixture comprising para-xylene, meta-xylene, ortho-xylene, and ethylbenzene under substantially isothermal conditions, said pressure swing adsorption process comprising:

(a) adsorbing the mixture onto an adsorbent defining non-selective voids and comprising a para-selective adsorbent capable of selectively adsorbing para-xylene at a temperature and pressure at which at least 0.01 grams of para-xylene may be adsorbed per gram of adsorbent;

(b) producing a first effluent stream comprising a mixture of ortho-xylene and meta-xylene which contains no more than a total of about 25 mole percent of para-xylene;

(c) selectively removing a portion of the mixture from the non-selective voids;

(d) selectively desorbing para-xylene from the adsorbent by decreasing partial pressure of para-xylene; and (e) collecting a para-xylene-rich stream comprising the para-xylene from Step (d) which contains no more than a total of about 50 mole percent of meta-xylene and ortho-xylene based on total $C_8$ aromatics.

2. The process of claim 1 wherein the para-selective adsorbent used in the pressure swing adsorption process comprises a para-selective, non-acidic molecular sieve.

3. The process of claim 1 wherein the para-selective adsorbent used in the pressure swing adsorption process comprises a para-selective, non-acidic, medium pore molecular sieve.

4. The process of claim 3 wherein the molecular sieve used in the pressure swing adsorption process comprises orthorhombic crystals of silicalite having an average minimum dimension of at least about 0.2 $\mu$m.

5. The process of claim 1 wherein the pressure swing adsorption in step (3) is operated at a temperature of at least about 350° F. and a pressure of at least about 30 psia.

6. The process of claim 1 wherein the pressure swing adsorption in step (3) is operated at a temperature of from about 350° F. to about 750° F. and a pressure of from about 30 psia to about 400 psia.

7. The process of claim 1 wherein the pressure swing adsorption in step (3) is operated at a temperature of from about 400° F. to about 650° F. and a pressure of from about 50 psia to about 300 psia.

8. The process of claim 1 wherein at least a portion of the meta-xylene and ortho-xylene stream produced by pressure swing adsorption in (3)(b) is contacted with an isomerization catalyst and isomerized to produce an isomerizate comprising an equilibrium mixture of xylenes.

9. The process of claim 8 and wherein at least a portion of the isomerizate is recycled to separation step (2).

10. The process of claim 8 wherein at least a portion of the isomerizate is recycled to pressure swing adsorption step (3).

11. The process of claim 1 wherein the stream comprising para-xylene which contains no more than a total of about 50 mole percent of meta-xylene and ortho-xylene based on total $C_8$ aromatics obtained in step (3)(e) is further purified using a process selected from crystallization and simulated moving bed adsorption chromatography to produce a para-xylene product stream and a reject stream comprising meta-xylene, ortho-xylene, and ethylbenzene.

12. The process of claim 11 wherein at least a portion of the reject stream comprising meta-xylene, ortho-xylene, and ethylbenzene is contacted with an isomerization catalyst and isomerized to produce an isomerizate comprising an equilibrium mixture of xylenes.

13. The process of claim 12 wherein at least a portion of the isomerizate is recycled to pressure swing adsorption step (3).

14. The process of claim 11 wherein at least a portion of the meta-xylene and ortho-xylene stream produced by the pressure swing adsorption process in step (3)(b) is combined with at least a portion of the reject stream comprising meta-xylene, ortho-xylene, and ethylbenzene from the purification process, and the combined streams are contacted with an isomerization catalyst and isomerized to produce an isomerizate comprising an equilibrium mixture of xylenes.

15. The process of claim 14 wherein at least a portion of the isomerizate is recycled to separation step (2).

16. The process of claim 11 wherein at least a portion of the meta-xylene and ortho-xylene stream produced by pressure swing adsorption in step (3)(b) is contacted with an isomerization catalyst and isomerized to produce an isomerizate comprising an equilibrium mixture of xylenes which is, optionally, recycled to pressure swing adsorption step (3), and wherein at least a portion of the reject stream comprising meta-xylene, ortho-xylene, and ethylbenzene from the purification process is contacted with an ethylbenzene conversion catalyst and to produce an effluent comprising an equilibrium mixture of xylenes which is, optionally, recycled to separation step (2).

17. The process of claim 1 wherein the mixture of ortho-xylene and meta-xylene produced in step (1 b) contains no more than a total of about 15 mole percent of para-xylene and ethylbenzene based on total $C_8$ aromatics, and the stream containing para-xylene and ethylbenzene collected in step (1 e) contains no more than a total of about 25 mole percent of meta-xylene and ortho-xylene based on total $C_8$ aromatics.

18. The process of claim 1 wherein the pressure swing adsorption in step (3) comprises a pressure swing adsorption process for separating para-xylene and ethylbenzene from the feed wherein the feed further comprises a gaseous mixture comprising $C_8$ aromatics containing para-xylene, ethylbenzene, meta-xylene and ortho-xylene under substantially isothermal conditions comprising:

(a) adsorbing the mixture onto an adsorbent defining non-selective voids comprising a para-selective adsorbent capable of selectively adsorbing para-xylene and ethylbenzene at a temperature and pressure at which at least 0.01 grams of para-xylene and ethylbenzene may be adsorbed per gram of adsorbent;

(b) producing a first effluent stream comprising a mixture of ortho-xylene and meta-xylene, which contains no more than a total of about 25 mole percent para-xylene and ethylbenzene based on total $C_8$ aromatics;

(c) selectively removing a portion of the mixture from the non-selective voids;

(d) selectively desorbing para-xylene and ethylbenzene from the adsorbent by decreasing partial pressure of para-xylene and ethylbenzene; and (e) collecting a stream comprising the para-xylene and ethylbenzene from Step (d) which contains no more than a total of about 50 mole percent of meta-xylene and ortho-xylene based on total $C_8$ aromatics.

19. The process of claim 18 wherein the adsorbent comprises a para-selective, non-acidic, medium pore molecular sieve, the temperature is from about 350° F. to about 750° F., and the pressure is from about 30 psia to about 400 psia.

20. The process of claim 18 wherein the mixture of ortho-xylene and meta-xylene produced in step (1 b) contains no more than a total of about 15 mole percent of para-xylene and ethylbenzene based on total $C_8$ aromatics, and the stream containing para-xylene and ethylbenzene collected in step (1e) contains no more than a total of about 25 mole percent of meta-xylene and ortho-xylene based on total $C_8$ aromatics.

21. A process for the production of para-xylene from a feed comprising toluene comprising:
   (1) subjecting the toluene feed to toluene conversion to produce a xylene-containing effluent stream comprising para-xylene, meta-xylene, ortho-xylene, ethylbenzene, unreacted toluene, and other unconverted reactants;
   (2) separating unreacted toluene and such other unconverted reactants from the xylene-containing effluent stream from step (1) to produce a para-xylene-containing stream comprising para-xylene, meta-xylene, ortho-xylene, and ethylbenzene and converting the para-xylene-containing stream to a gaseous mixture comprising para-xylene, meta-xylene, ortho-xylene, and ethylbenzene; and
   (3) subjecting the gaseous mixture to a pressure swing adsorption process for separating para-xylene and ethylbenzene from a feed comprising the gaseous mixture comprising $C_8$ aromatics containing para-xylene, ethylbenzene, meta-xylene and ortho-xylene under substantially isothermal conditions comprising:
      (a) providing an adsorbent bed comprising a para-selective adsorbent which exhibits capacity to selectively adsorb and desorb para-xylene and ethylbenzene under substantially isothermal conditions at operating pressure, disposed in a vessel having at least one inlet and at least one outlet such that gas entering an inlet passes through the adsorbent bed to an outlet, and containing a purge gas substantially free of $C_8$ aromatic compounds;
      (b) flowing a gaseous feed mixture comprising xylenes and ethylbenzene into the adsorbent bed through one or more of the vessel inlets, and collecting effluent from one or more of the outlets and segregating at least a fraction of the purge gas substantially free of $C_8$ aromatic compounds while selectively adsorbing para-xylene and ethylbenzene from the gaseous feed mixture under substantially isothermal conditions in the bed;
      (c) collecting from one or more of the outlets a first effluent product comprising m-xylene and o-xylene which contains no more than a total of about 25 mole percent of para-xylene and ethylbenzene based on total $C_8$ aromatics;
      (d) replacing the feed mixture flowing into the adsorbent bed though one or more inlets with the purge gas while maintaining substantially isothermal conditions in the adsorbent bed, and collecting from one or more of the outlets an effluent gaseous mixture until effluent at the outlet contains no more than a total of about 50 mole percent of m-xylene and o-xylene based on total $C_8$ aromatics;
      (e) collecting from one or more of the outlets a second effluent product comprising ethylbenzene and para-xylene which contains no more than a total of about 50 mole percent of m-xylene and o-xylene based on total $C_8$ aromatics; and
      (f) repeating steps (b) through (e).

22. The process of claim 21 wherein the adsorbent comprises a para-selective, non-acidic, medium pore molecular sieve, the temperature is from about 350° F. to about 750° F., the pressure is from about 30 psia to about 400 psia, and the purge gas is selected from the group consisting of $C_1$–$C_4$ alkanes, He, $CO_2$, hydrogen, nitrogen, argon and mixtures thereof.

23. The process of claim 21 wherein the mixture of ortho-xylene and meta-xylene produced in step (b) contains no more than a total of about 15 mole percent of para-xylene and ethylbenzene based on total $C_8$ aromatics, and the stream containing para-xylene and ethylbenzene collected in step (e) contains no more than a total of about 25 mole percent of meta-xylene and ortho-xylene based on total $C_8$ aromatics.

24. The process of claim 21 wherein the steps (b) through (e) are carried out under substantially isothermal conditions at temperatures in a range upward from about 450° F., wherein steps (b) through (e) are carried out under constant pressure at a pressure of at least about 80 psia, and wherein steps (b) through (e) are repeated with a cycle time of from about 2 minutes to about 200 minutes.

25. The process of claim 21 wherein at least a portion of the effluent gaseous mixture collected in step (d) is admixed with the gaseous feed mixture in subsequent cycles.

26. The process of claim 21 wherein the purge gas comprises hydrogen, and wherein steps (b) through (e) are repeated with a cycle time of from about 3 minutes to about 30 minutes under substantially isothermal conditions at a temperature of about 350° F. to about 750° F. and at constant operating pressure at a pressure of at least about 30 psia.

27. The process of claim 21 wherein the flow of said purge gas is counter current to the flow of said gaseous feed mixture.

28. A process for the production of para-xylene from a feed comprising toluene comprising:
   (1) subjecting the toluene feed to toluene conversion to produce a xylene-containing effluent stream comprising para-xylene, meta-xylene, ortho-xylene, ethylbenzene, unreacted toluene, and other unconverted reactants;
   (2) separating unreacted toluene and such other unconverted reactants from the xylene-containing effluent stream from step (1) to produce a para-xylene-containing stream comprising para-xylene, meta-xylene, ortho-xylene, and ethylbenzene and converting the para-xylene-containing stream to a gaseous mixture comprising para-xylene, meta-xylene, ortho-xylene, and ethylbenzene; and
   (3) subjecting the gaseous mixture to a pressure swing adsorption process for separating para-xylene and ethylbenzene from a feed comprising the gaseous mixture comprising $C_8$ aromatics containing para-xylene, ethylbenzene, meta-xylene and ortho-xylene under substantially isothermal conditions comprising:
      (a) providing an adsorbent bed comprising a para-selective adsorbent which exhibits capacity to selectively adsorb and desorb para-xylene and ethylbenzene under substantially isothermal conditions at operating pressure, disposed in a vessel having at least one inlet and at least one outlet such that gas entering an inlet passes through the particulate bed to an outlet and pressurizing the vessel with a mixture comprising meta-xylene and ortho-xylene to a preselected pressure for adsorption;

(b) flowing a gaseous feed mixture comprising xylene isomers and ethylbenzene into the adsorbent bed through one or more inlets and displacing the meta-xylene and ortho-xylene in the vessel while selectively adsorbing ethylbenzene and para-xylene from the gaseous feed mixture under substantially isothermal conditions in the adsorbent bed;

(c) collecting from one or more of the outlets a first effluent product comprising meta-xylene and ortho-xylene which contains no more than a total of about 25 mole percent of ethylbenzene and para-xylene based on total $C_8$ aromatics while maintaining substantially isothermal conditions in the adsorbent bed and the flow of feed at the pressure for adsorption;

(d) replacing the feed mixture flowing into the bed though one or more inlets with a purge gas comprising para-xylene and ethylbenzene substantially free of meta-xylene and ortho-xylene while maintaining the pressure for adsorption and substantially isothermal conditions in the bed, and collecting from one or more of the outlets a gaseous mixture comprising feed;

(e) reducing the pressure to desorb ethylbenzene and para-xylene while maintaining substantially isothermal conditions in the adsorbent bed; and (f) collecting a second effluent product comprising at least a portion of the ethylbenzene and para-xylene from step (e) which contains no more than a total of about 50 mole percent of meta-xylene and ortho-xylene based on total $C_8$ aromatics.

29. The process of claim 28 wherein the flow of said para-xylene and ethylbenzene purge gas is countercurrent to the flow of the gaseous feed mixture.

30. The process of claim 28 wherein the para-xylene and ethylbenzene effluent flow during depressurization is countercurrent to the flow of the gaseous feed mixture.

31. The process of claim 28 wherein the flow of meta-xylene and ortho-xylene to pressurize the vessel is countercurrent to the feed gas flow.

32. A process for the production of para-xylene from a feed comprising toluene comprising:

(1) subjecting the toluene feed to toluene conversion to produce a xylene-containing effluent stream comprising para-xylene, meta-xylene, ortho-xylene, ethylbenzene, unreacted toluene, and other unconverted reactants;

(2) separating unreacted toluene and such other unconverted reactants from the xylene-containing effluent stream from step (1) to produce a para-xylene-containing stream comprising para-xylene, meta-xylene, ortho-xylene, and ethylbenzene and converting the para-xylene-containing stream to a gaseous mixture comprising para-xylene, meta-xylene, ortho-xylene, and ethylbenzene; and (3) subjecting the gaseous mixture to a pressure swing adsorption process for separating para-xylene and ethylbenzene from a feed comprising the gaseous mixture comprising $C_8$ aromatics containing para-xylene, ethylbenzene, meta-xylene and ortho-xylene under substantially isothermal conditions comprising:

(a) providing at least two adsorbent beds containing an adsorbent comprising a para-selective adsorbent defining non-selective voids which exhibits capacity to selectively adsorb and desorb para-xylene and ethylbenzene under substantially isothermal conditions at operating pressure, disposed in connected vessels, each having at least one inlet and at least one outlet such that gas entering an inlet passes through the particulate bed to an outlet, and pressurizing a first vessel with a mixture comprising meta-xylene and ortho-xylene to a preselected pressure for adsorption;

(b) flowing a gaseous feed mixture comprising xylene isomers and ethylbenzene into the adsorbent bed in the first vessel though one or more inlets and displacing the meta-xylene and ortho-xylene in the vessel while selectively adsorbing ethylbenzene and para-xylene from the gaseous feed mixture under substantially isothermal conditions in the adsorbent bed;

(c) collecting from one or more of the outlets a first effluent product comprising meta-xylene and ortho-xylene which contains no more than a total of about 25 mole percent of ethylbenzene and para-xylene based on total $C_8$ aromatics while maintaining substantially isothermal conditions in the adsorbent bed and the flow of feed at the pressure for adsorption;

(d) stopping the flow of feed and reducing the pressure in the first vessel sufficiently to permit removal of at least a portion of the feed from non-selective voids while maintaining substantially isothermal conditions in the bed by equalizing the pressure in the first vessel with the pressure in the second vessel which is at a lower pressure;

(e) further reducing the pressure in the first vessel to desorb ethylbenzene and para-xylene while maintaining substantially isothermal conditions in the bed; and (f) collecting a second effluent product comprising ethylbenzene and para-xylene which contains no more than a total of about 50 mole percent of meta-xylene and ortho-xylene based on total $C_8$ aromatics.

33. The process of claim 32 wherein, following step (1f), a purge gas comprising meta-xylene and ortho-xylene is added to the first vessel to displace para-xylene and ethylbenzene in the non-selective voids, and an effluent comprising the para-xylene and ethylbenzene is collected.

34. The process of claim 32 wherein prior to step (1d) a rinse comprising para-xylene and ethylbenzene is introduced into the vessel to displace meta-xylene and ortho-xylene in non-selective voids.

35. The process of claim 1 wherein the pressure swing adsorption in step (a) comprises a pressure swing adsorption process for separating para-xylene and ethylbenzene from a feed comprising a gaseous mixture comprising $C_8$ aromatics containing para-xylene, ethylbenzene, meta-xylene and ortho-xylene under substantially isothermal conditions comprising:

(a) providing an adsorbent bed comprising a para-selective adsorbent which exhibits capacity to selectively adsorb and desorb para-xylene and ethylbenzene under substantially isothermal conditions at operating pressure, disposed in a vessel having at least one inlet and at least one outlet such that gas entering an inlet passes through the particulate bed to an outlet and pressurizing the vessel with a mixture comprising meta-xylene and ortho-xylene to a preselected pressure for adsorption;

(b) flowing a gaseous feed mixture comprising xylene isomers and ethylbenzene into the adsorbent bed though one or more inlets and displacing the meta-xylene and ortho-xylene in the vessel while selectively adsorbing ethylbenzene and para-xylene from the gaseous feed mixture under substantially isothermal conditions in the adsorbent bed;

(c) collecting from one or more of the outlets a first effluent product comprising meta-xylene and ortho-xylene which contains no more than a total of about 25 mole percent of ethylbenzene and para-xylene based on total $C_8$ aromatics while maintaining substantially isothermal conditions in the adsorbent bed and the flow of feed at the pressure for adsorption;

(d) stopping the flow of feed and reducing operating pressure to a pressure at which para-xylene and ethylbenzene desorb while maintaining substantially isothermal conditions in the adsorbent bed; and (e) collecting a second effluent product comprising at least a portion of the ethylbenzene and para-xylene desorbed from the para-selective adsorbent in step (d) which contains no more than a total of about 50 mole percent of meta-xylene and ortho-xylene based on total $C_8$ aromatics.

36. The process of claim 35 wherein, following step (e), a purge gas of meta-xylene and ortho-xylene is added to the first vessel to displace para-xylene and ethylbenzene in the non-selective voids, and an effluent comprising the para-xylene and ethylbenzene is collected.

37. The process of claim 1 wherein the xylene-containing effluent stream produced in the toluene conversion process contains para-xylene at a concentration greater than the equilibrium concentration.

38. The process of claim 1 wherein the xylene-containing effluent stream produced in the toluene conversion process contains greater than 50 wt % para-xylene.

39. The process of claim 1 wherein the xylene-containing effluent stream produced in the toluene conversion process contains greater than 75 wt % para-xylene.

40. A process for the production of para-xylene from a feed comprising toluene comprising:

(1) subjecting the toluene feed to toluene conversion to produce a xylene-containing effluent stream comprising para-xylene, meta-xylene, ortho-xylene, ethylbenzene, and unreacted toluene, (2) separating unreacted toluene and any and other unconverted reactants from the xylene-containing effluent stream from step (1) to produce a para-xylene-containing stream comprising para-xylene, meta-xylene, ortho-xylene, and ethylbenzene and converting the para-xylene-containing stream to a gaseous mixture comprising para-xylene, meta-xylene, ortho-xylene, and ethylbenzene; and (3) subjecting the gaseous mixture to a pressure swing adsorption process for separating para-xylene from a feed comprising a gaseous mixture comprising para-xylene, meta-xylene, ortho-xylene, and ethylbenzene under substantially isothermal conditions, said pressure swing adsorption process comprising:

(a) adsorbing the mixture onto an adsorbent comprising a para-selective adsorbent defining non-selective voids capable of selectively adsorbing from the gaseous mixture para-xylene at a temperature and pressure at which at least 0.01 grams of para-xylene may be adsorbed per gram of adsorbent;

(b) collecting from step (a) a first effluent stream having an enriched concentration of ortho-xylene and meta-xylene;

(c) selectively removing at least a portion of the gaseous mixture from the non-selective voids;

(d) selectively desorbing para-xylene from the para-selective adsorbent by decreasing partial pressure of para-xylene; and (e) collecting a at least a portion of the para-xylene from step (d) as a para-xylene-rich stream having an enriched concentration of para-xylene.

41. The process of claim 40 wherein the adsorbent used in the pressure swing adsorption comprises a para-selective, non-acidic, medium pore molecular sieve, and wherein the pressure swing adsorption in step is operated at a temperature of at least about 350° F. and a pressure of at least about 30 psia.

42. The process of claim 3 wherein the para-selective, non-acidic medium pore molecular sieve is selected from the group of molecular sieve structure types consisting of MFI, TON, MTT, EUO, MEL, and FER.

43. The process of claim 1 wherein the adsorbent contains about 5 to about 100 weight percent para-selective adsorbent.

* * * * *